(12) United States Patent
Zhu et al.

(10) Patent No.: US 7,071,200 B2
(45) Date of Patent: Jul. 4, 2006

(54) GONADOTROPIN-RELEASING HORMONE RECEPTOR ANTAGONISTS AND METHODS RELATING THERETO

(75) Inventors: Yun-Fei Zhu, San Diego, CA (US); Collin Regan, San Diego, CA (US); Jaimie K. Rueter, San Diego, CA (US); Zhiqiang Guo, San Diego, CA (US); Yongsheng Chen, San Diego, CA (US); Charles Q. Huang, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 10/885,511

(22) Filed: Jul. 6, 2004

(65) Prior Publication Data

US 2005/0043338 A1    Feb. 24, 2005

Related U.S. Application Data

(60) Provisional application No. 60/485,436, filed on Jul. 7, 2003.

(51) Int. Cl.
*C07D 239/54*    (2006.01)
*A61K 31/513*    (2006.01)

(52) U.S. Cl. ...................... 514/274; 544/311
(58) Field of Classification Search ............... 544/311; 514/274
See application file for complete search history.

(56) References Cited

U.S. PATENT DOCUMENTS

| 6,608,197 | B1 | 8/2003 | Zhu et al. ............ 544/309 |
|---|---|---|---|
| 6,872,728 | B1 * | 3/2005 | Zhu et al. ............ 514/269 |
| 2005/0038056 | A1 | 2/2005 | Huang et al. ............ 514/269 |
| 2005/0038057 | A1 | 2/2005 | Guo et al. ............ 514/269 |

FOREIGN PATENT DOCUMENTS

| WO | WO 96/38438 | 12/1996 |
|---|---|---|
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | WO 00/69859 | 11/2000 |
| WO | WO 01/29044 A1 | 4/2001 |
| WO | WO 01/55119 A2 | 8/2001 |
| WO | WO 02/11732 A1 | 2/2002 |
| WO | WO 02/066459 A1 | 8/2002 |
| WO | WO 03/011293 A2 | 2/2003 |
| WO | WO 03/011839 A1 | 2/2003 |
| WO | WO 03/011841 A1 | 2/2003 |
| WO | WO 03/011870 A1 | 2/2003 |
| WO | WO 03/013528 A1 | 2/2003 |

OTHER PUBLICATIONS

Simone, Oncology: Introduction, Cecil Textbook of Medicine, 20th Edition, vol. 1, pp. 1004-1010, 1996.*
Huime et al., PubMed Abstract (Lancet 358(9295):1793-803) Nov. 2001.*
McCartney et al., PubMed Abstract (Semin Reprod Med. 20(4):317-26) Nov. 2002.*
Olivennes et al., PubMed Abstract (Hum Reprod Update 8(3):279-90) May-Jun. 2002.*
Cho, N., et al. "Discovery of a Novel, Potent, and Orally Active Nonpeptide Antagonist of the Human Luteinizing Hormone-releasing Hormone (LHRH) Receptor," *J. Med. Chem.* 41(22):4190-5, Oct. 22, 1998.
Zhu, Y-F., et al., "Identification of 1-arylmethyl-3-(2-aminoethyl)-5-aryluracil as Novel Gonadotrop-releasing Hormone Receptor Antagonists," *J. Med. Chem.*; 46(11):2023-6, May 22, 2003.

* cited by examiner

*Primary Examiner*—Deepak Rao
(74) *Attorney, Agent, or Firm*—Seed IP Law Group PLLC

(57) ABSTRACT

GnRH receptor antagonists are disclosed that have utility in the treatment of a variety of sex-hormone related conditions in both men and women. The compounds of this invention have the structure:

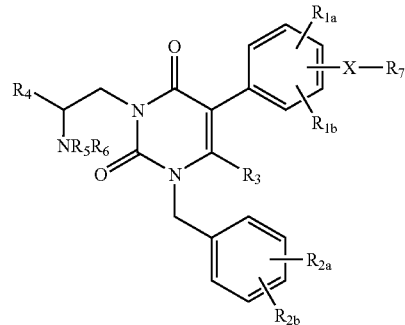

wherein $R_{1a}$, $R_{1b}$, $R_{2a}$, $R_{2b}$, $R_3$, $R_4$, $R_5$, $R_6$, $R_7$ and X are as defined herein, including stereoisomers, prodrugs and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

39 Claims, No Drawings

SEQUENCE LISTING

```
<160> NUMBER OF SEQ ID NOS: 2

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide GnRH agonist.
<220> FEATURE:
<221> NAME/KEY: MOD_RES
<222> LOCATION: 6
<223> OTHER INFORMATION: D-Leucine

<400> SEQUENCE: 2

Glu His Trp Ser Tyr Leu Leu Arg Pro
 1               5
```

GONADOTROPIN-RELEASING HORMONE RECEPTOR ANTAGONISTS AND METHODS RELATING THERETO

CROSS-REFERENCE TO RELATED APPLICATION

This application claims the benefit of U.S. Provisional Patent Application No. 60/485,436 filed Jul. 7, 2003, which application is incorporated herein by reference in its entirety.

STATEMENT OF GOVERNMENT INTEREST

Partial funding of the work described herein was provided by the U.S. Government under Grant No. 1-R43-HD38625 and 2R44-HD38625-02 provided by the National Institutes of Health. The U.S. Government may have certain rights in this invention.

BACKGROUND OF THE INVENTION

1. Field of the Invention

This invention relates generally to gonadotropin-releasing hormone (GnRH) receptor antagonists, and to methods of treating disorders by administration of such antagonists to a warm-blooded animal in need thereof.

2. Description of the Related Art

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH2) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine leiomyoma (fibroids), ovarian cancer, prostatic hyperplasia, assisted reproductive therapy, and precocious puberty (*The Lancet* 358:1793–1803, 2001; *Mol. Cell. Endo.* 166:9–14, 2000). For example, peptidic GnRH agonists, such as leuprorelin (pGlu-His-Trp-Ser-Tyr-d-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780,437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GnRH receptor antagonists; published PCTs WO97/14682, 97/14697 and 99/09033 disclose quinoline and thienopyridine derivatives as GnRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists. Recently published PCTs WO 02/066459 and WO 02/11732 disclose the use of indole derivatives and novel bicyclic and tricyclic pyrrolidine derivatives as GnRH antagonists, respectively. Other recently published PCTs which disclose compounds and their use as GnRH antagonists include WO 00/69859, WO 01/29044, WO 01/55119, WO 03/013528, WO 03/011870, WO 03/011841, WO 03/011839 and WO 03/011293.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

BRIEF SUMMARY OF THE INVENTION

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

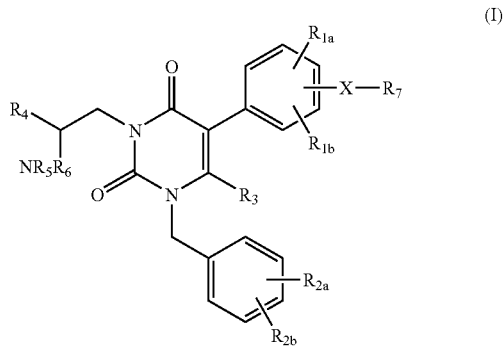

(I)

including stereoisomers, prodrugs and pharmaceutically acceptable salts thereof, wherein $R_{1a}$, $R_{1b}$, $R_{2a}$, $R_{2b}$, $R_3$, $R_4$, $R_5$, $R_6$, $R_7$ and X are as defined below.

The GnRH receptor antagonists of this invention have utility over a wide range of therapeutic applications, and may be used to treat a variety of sex-hormone related conditions in both men and women, as well as a mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The compounds of the present invention, in addition to their GnRH receptor antagonist activity, possess a reduced interaction with the major metabolic enzymes in the liver, namely the Cytochrome P450 enzymes. This family of enzymes, which includes the subtypes CYP2D6 and CYP3A4, is responsible for the metabolism of drugs and toxins leading to their disposition from the body. Inhibition of these enzymes can lead to life-threatening conditions where the enzyme is not able to perform this function.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

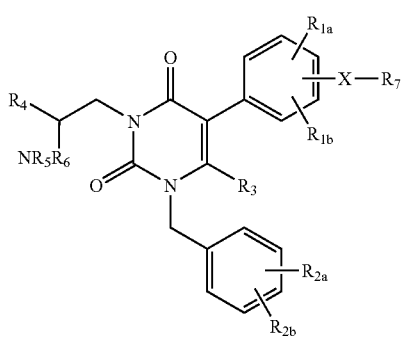

(I)

or a stereoisomer, prodrug or pharmaceutically acceptable salt thereof,
wherein:
$R_{1a}$ and $R_{1b}$ are the same or different and independently hydrogen, halogen, $C_{1-4}$alkyl, or alkoxy;

$R_{2a}$ and $R_{2b}$ are the same or different and independently hydrogen, halogen, trifluoromethyl, cyano or —$SO_2CH_3$;
$R_3$ is hydrogen or methyl;
$R_4$ is phenyl or $C_{3-7}$alkyl;
$R_5$ and $R_6$ are the same or different and independently hydrogen or $C_{1-4}$alkyl; or
$R_5$ and the nitrogen to which it is attached taken together with $R_4$ and the carbon to which it is attached form 1,2,3,4-tetrahydroisoquinoline or 2,3-dihydro-1H-isoindole;
$R_7$ is —COOH or an acid isostere; and
X is —O—($C_{1-6}$alkanediyl) or —O—($C_{1-6}$alkanediyl)—O—($C_{1-6}$alkanediyl) wherein each ($C_{1-6}$alkanediyl) is optionally substituted with from 1 to 3 $C_{1-4}$alkyl groups.

As used herein, the above terms have the following meaning:

"$C_{1-6}$alkyl" means a straight chain or branched, noncyclic or cyclic, unsaturated or saturated aliphatic hydrocarbon containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-4}$alkyl" means a straight chain or branched, noncyclic or cyclic hydrocarbon containing from 1 to 4 carbon atoms. Representative straight chain alkyls include methyl, ethyl, n-propyl, n-butyl, and the like; branched alkyls include isopropyl, sec-butyl, isobutyl, tert-butyl, and the like; while cyclic alkyls include cyclopropyl and the like.

"$C_{3-7}$alkyl" means a straight chain or branched, noncyclic or cyclic hydrocarbon containing from 3 to 7 carbon atoms. Representative straight chain alkyls include n-propyl, n-butyl, n-hexyl, and the like; while branched alkyls include isopropyl, sec-butyl, isobutyl, tert-butyl, isopentyl, and the like. Representative cyclic alkyls include cyclopropyl, cyclopentyl, cyclohexyl, and the like.

"$C_{1-6}$alkanediyl" means a divalent $C_{1-6}$alkyl from which two hydrogen atoms are taken from the same carbon atom or from difference carbon atoms, such as —$CH_2$—, —$CH_2CH_2$—, —$CH_2CH_2CH_2$—, —$CH(CH_3)CH_2CH_2$—, —$CH_2C(CH_3)_2CH_2$—, and the like.

"Halogen" means fluoro, chloro, bromo or iodo, typically fluoro and chloro.

"Hydroxy" means —OH.

"Alkoxy" means —O—($C_{1-6}$alkyl).

"Cyano" means —CN.

"Acid isostere" means a moiety that exhibits properties similar carboxylic acid, and which has a pKa of less than 8 and preferably less than 7. Representative acid isosteres include tetrazole, 3H-[1,3,4]oxadiazol-2-one, [1,2,4]oxadiazol-3-one, 1,2-dihydro-[1,2,4]triazol-3-one, 2H-[1,2,4]oxadiazol-5-one, triazole substituted with a sulfonyl or sulfoxide group, imidazole substituted with a sulfonyl or sulfoxide group, [1,2,4]-oxadiazolidine-3,5-dione, [1,2,4]-thiadiazolidine-3,5-dione, imidazolidine-2,4-dione, imidazolidine-2,4,5-trione, pyrrolidine-2,5-dione and pyrrolidine-2,3,5-trione. Acid isosteres also include —C(=O)NHSO$_2$NR$_a$R$_b$, —C(=O)NHSO$_2$R$_b$, —C(=O)NHC(=O)NR$_a$R$_b$ and —C(=O)NHC(=O)R$_b$, where R$_a$ is hydrogen or C$_{1-4}$alkyl and R$_b$ is C$_{1-4}$alkyl.

In one embodiment of the invention, R$_4$ is phenyl and representative GnRH antagonists of the present invention include compounds having the following structure (II).

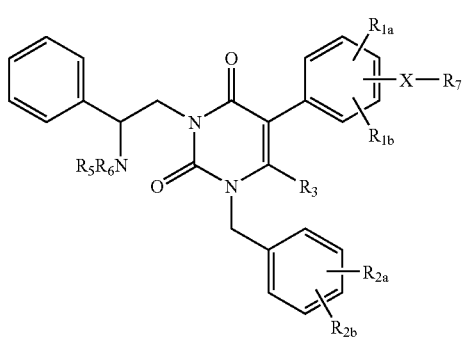

(II)

In another embodiment, R$_4$ is C$_{3-7}$alkyl as shown in structure (III). The C$_{3-7}$alkyl group may be straight chain or branched alkyl such as isobutyl as shown in structure (IV) or cyclic alkyl such as cyclohexyl as shown in structure (V).

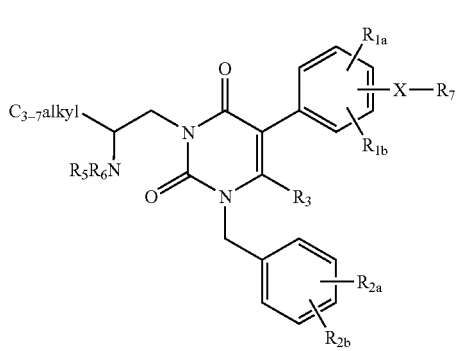

(III)

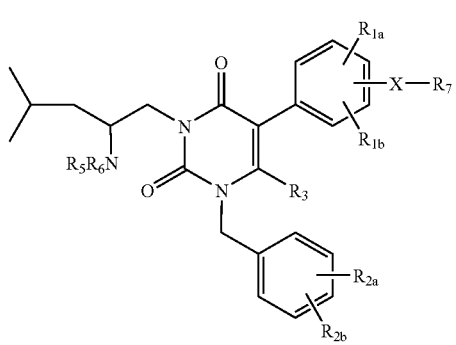

(IV)

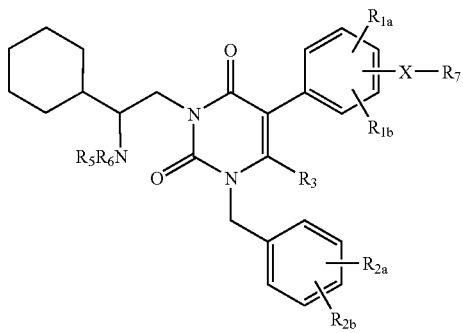

(V)

In another embodiment R$_5$ and the nitrogen to which it is attached taken together with R$_4$ and the carbon to which it is attached form 1,2,3,4-tetrahydroisoquinoline or 2,3-dihydro-1H-isoindole as shown in structures (VI) and (VII) respectively.

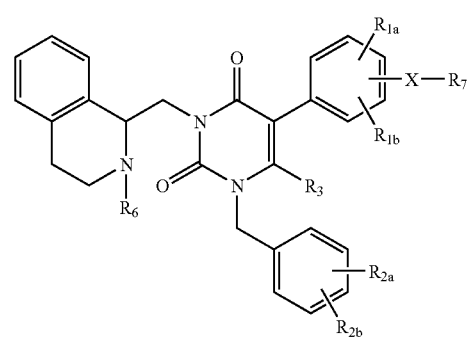

(VI)

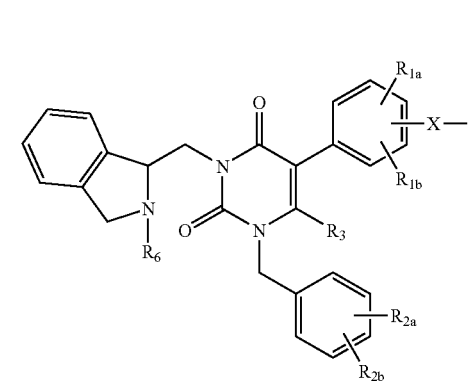

(VII)

In another embodiment, R$_{1a}$ and R$_{1b}$ are hydrogen, alkoxy or halogen. The alkoxy may be methoxy or ethoxy and the halogen is typically fluoro or chloro.

In another embodiment, R$_{2a}$ and R$_{2b}$ may be hydrogen, trifluoromethyl, halogen (typically fluoro or chloro) or —SO$_2$CH$_3$.

In further embodiments, X is —OCH$_2$CH$_2$—, —OCH$_2$CH$_2$CH$_2$— or —OCH$_2$CH$_2$CH$_2$CH$_2$—.

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

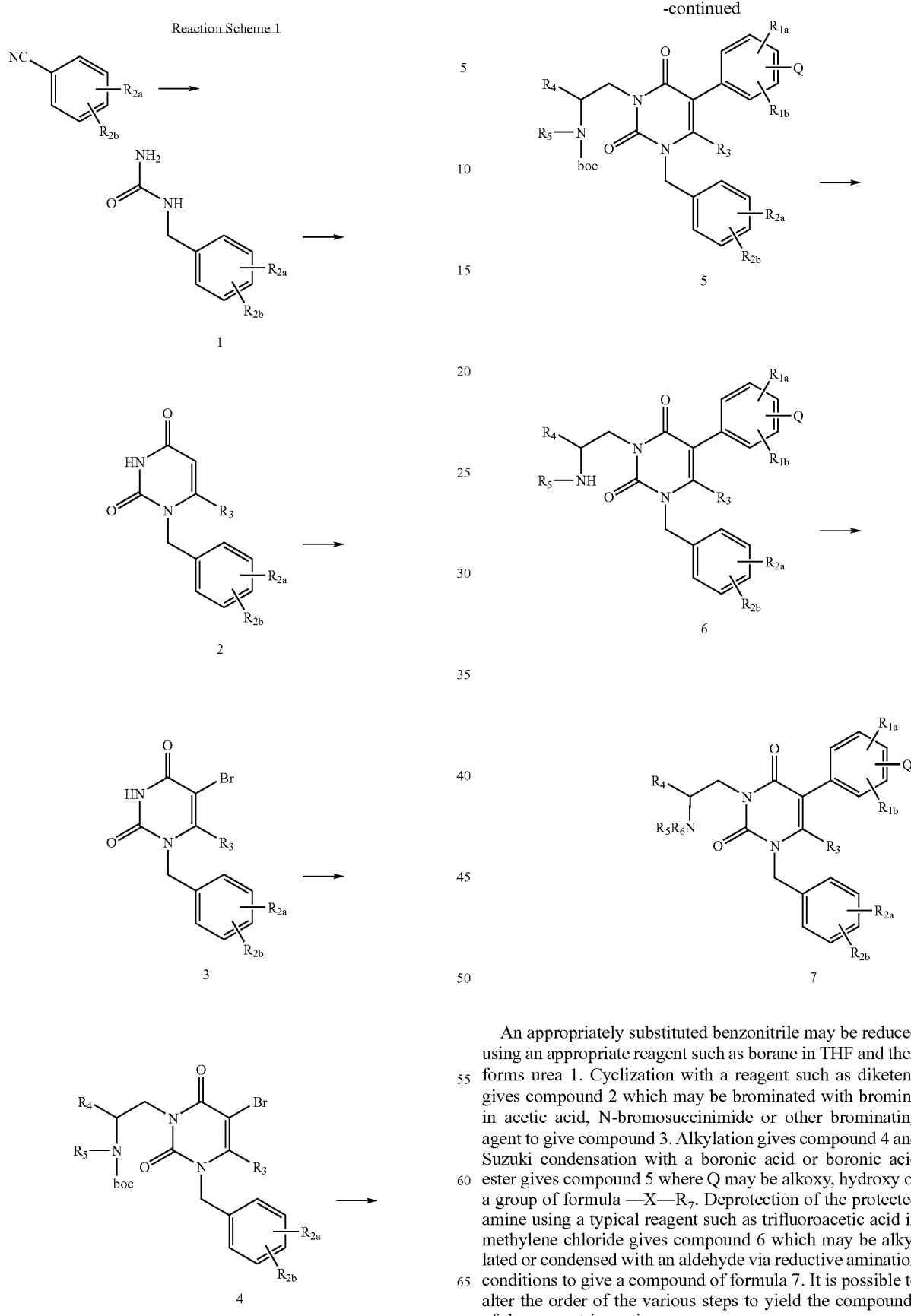

An appropriately substituted benzonitrile may be reduced using an appropriate reagent such as borane in THF and then forms urea 1. Cyclization with a reagent such as diketene gives compound 2 which may be brominated with bromine in acetic acid, N-bromosuccinimide or other brominating agent to give compound 3. Alkylation gives compound 4 and Suzuki condensation with a boronic acid or boronic acid ester gives compound 5 where Q may be alkoxy, hydroxy or a group of formula —X—$R_7$. Deprotection of the protected amine using a typical reagent such as trifluoroacetic acid in methylene chloride gives compound 6 which may be alkylated or condensed with an aldehyde via reductive amination conditions to give a compound of formula 7. It is possible to alter the order of the various steps to yield the compounds of the present invention.

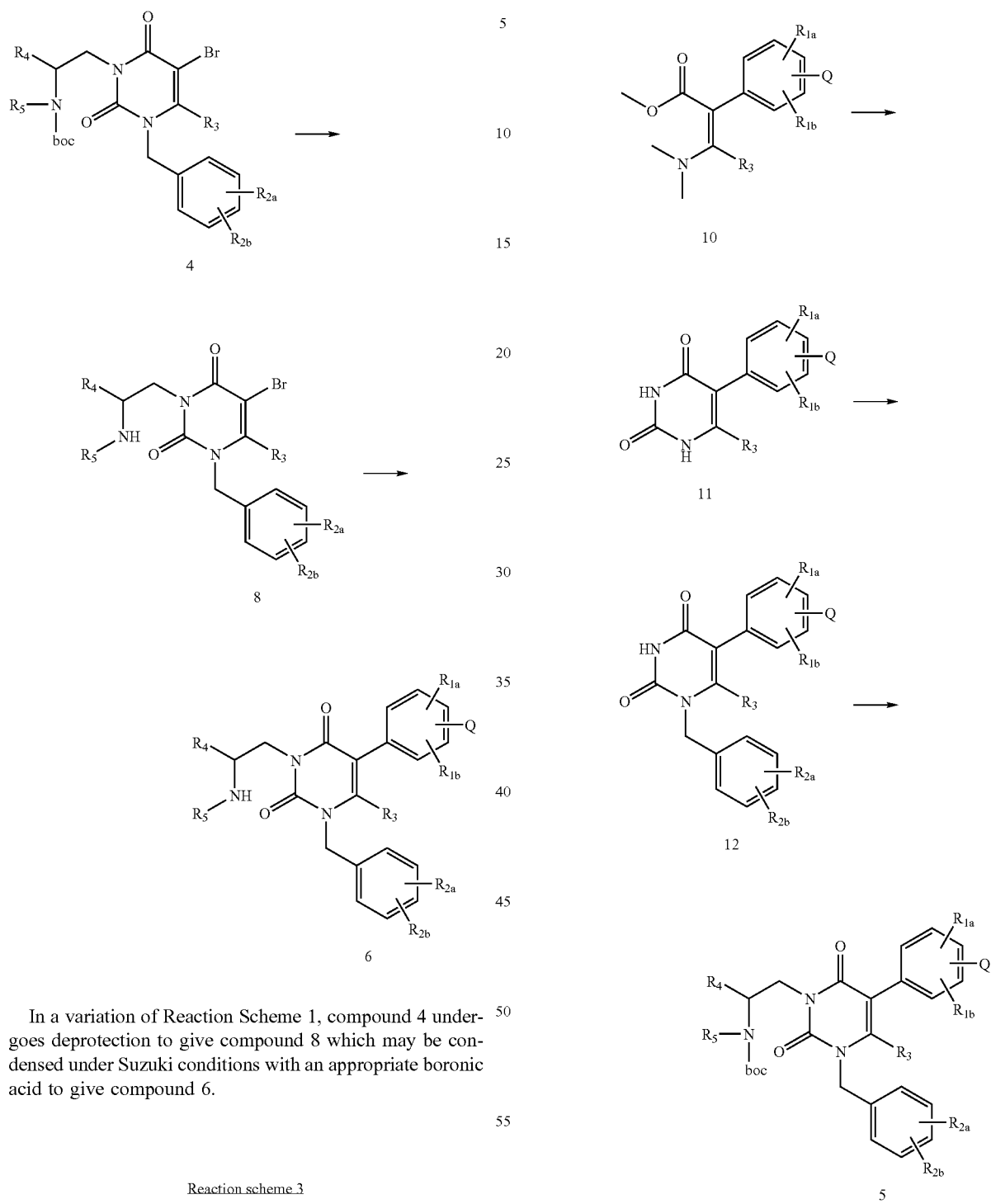

In a variation of Reaction Scheme 1, compound 4 undergoes deprotection to give compound 8 which may be condensed under Suzuki conditions with an appropriate boronic acid to give compound 6.

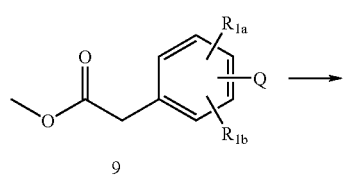

Substituted phenylacetic acid ester 9 (made from the corresponding acid or purchased) and reagent such as dimethylformamide dimethylacetal are condensed to give 10. Cyclization with urea gives a compound of formula 11. Alkylation using, for example, a substituted benzyl bromide gives 12 which may be alkylated with an appropriate alkyl halide, mesylate or tosylate to give 5.

Reaction Scheme 4

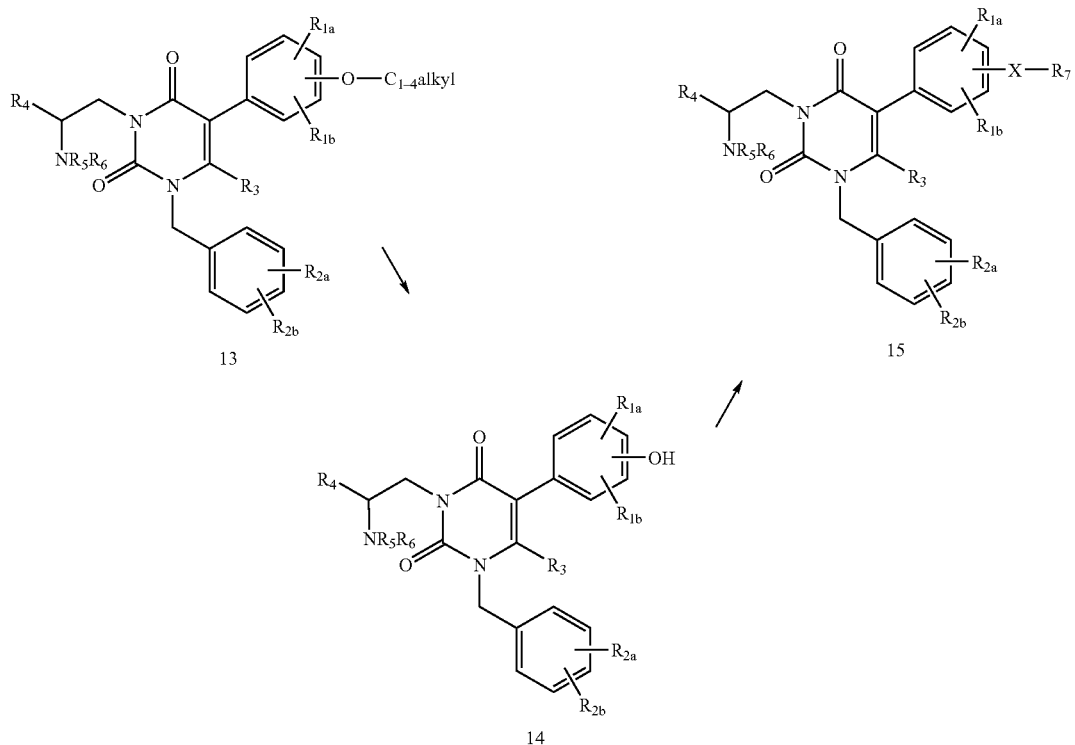

Compound 13 or the appropriated protected tert-butoxycarbonyl (Boc) or carbobenzyloxy (CBZ) version of Compound 13 may be dealkylated with an appropriate acid such as HBr or BBr$_3$ to give compound 14. Reprotection of the amine functionality may be necessary before alkylation with an alkyl halide which contains an acid, ester, or acid isostere functionality gives compound 15 directly, or may yield compound 15 following hydrolysis of the ester group if present.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the arnmonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay techniques. Assay techniques well known in the field include the use of cultured pituitary cells for measuring GnRH activity (Vale et al., *Endocrinology* 91:562–572, 1972) and the measurement of radioligand binding to rat pituitary membranes (Perrin et al., *Mol. Pharmacol.* 23:44–51, 1983) or to membranes from cells expressing cloned receptors as described below. Other assay techniques include (but are not limited to) measurement of the effects of GnRH receptor antagonists on the inhibition of GnRH-stimulated calcium flux, modulation of phosphoinositol hydrolysis, and the circulating concentrations of gonadotropins in the castrate animal. Descriptions of these techniques, the synthesis of radiolabeled ligand, the employment of radiolabeled ligand in radioimmunoassay, and the measurement of the effectiveness of a compound as a GnRH receptor antagonist follow.

Inhibition of GnRH Stimulated LH Release

Suitable GnRH antagonists are capable of inhibiting the specific binding of GnRH to its receptor and antagonizing activities associated with GnRH. For example, inhibition of GnRH stimulated LH release in immature rats may be measured according to the method of Vilchez-Martinez (*Endocrinology* 96:1130–1134, 1975). Briefly, twenty-five day old male Sprague-Dawley rats are administered an GnRH antagonist in saline or other suitable formulation by oral gavage, subcutaneous injection, or intravenous injection. This is followed by subcutaneous injection of 200 ng GnRH in 0.2 mL saline. Thirty minutes after the last injection, the animals are decapitated and trunk blood is collected. After centrifugation, the separated plasma is stored at −20° C. until determination of the concentrations of LH and/or FSH by radioimmunoassay (see below.)

Rat Anterior Pituitary Cell Culture Assay of GnRH Antagonists

Anterior pituitary glands are collected from 7-week-old female Sprague-Dawley rats and the harvested glands are digested with collagenase in a dispersion flask for 1.5 hr at 37° C. After collagenase digestion, the glands are further digested with neuraminidase for 9 min at 37° C. The digested tissue is then washed with 0.1% BSA/McCoy's 5A medium, and the washed cells are suspended in 3% FBS/0.1 BSA/McCoy's 5A medium and plated onto 96-well tissue culture plates at a cell density of 40,000 cells per well in 200 µl medium. The cells are then incubated at 37° C. for 3 days. For assay of an GnRH antagonist, the incubated cells are first washed with 0.1% BSA/McCoy's 5A medium once, followed by addition of the test sample plus 1 nM GnRH in 200 µl 0.1% BSA/McCoy's 5A medium in triplicate wells. Each sample is assayed at 5-dose levels to generate a dose-response curve for determination of the potency on the inhibition of GnRH stimulated LH and/or FSH release. After 4-hr incubation at 37° C., the medium is harvested and the level of LH and/or FSH secreted into the medium is determined by RIA.

Membrane Binding Assays 1

Cells stably, or transiently, transfected with GnRH receptor expression vectors are harvested, resuspended in 5% sucrose and homogenized using a polytron homogenizer (2×15 sec). Nucleii are removed by centrifugation (3000×g for 5 min.), and the supernatant is centrifuged (20,000×g for 30 min, 4° C.) to collect the membrane fraction. The final membrane preparation is resuspended in binding buffer (10 mM Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 µg protein in 130 ul binding buffer) to 50 µl of [$^{125}$I]-labeled GnRH peptide (~100,000 cpm) and 20 µl of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting. $K_i$ values are calculated from competition binding data using non-linear least squares regression using the Prism software package (GraphPad Software).

Membrane Binding Assays 2

For additional membrane binding assays, stably transfected HEK293 cells are harvested by striking tissue culture flasks against a firm surface and collected by centrifugation at 1000×g for 5 minutes. Cell pellets are resuspended in 5% sucrose and homogenized using a polytron homogenizer for two 15 second homogenization steps. Cell homogenates are then centrifuged for 5 minutes at 3000×g to remove nuclei, and the supernatant is subsequently centrifuged for 30 minutes at 44,000×g to collect the membrane fraction. The membrane pellet is resuspended in GnRH binding buffer (10 mM HEPES, pH 7.5, 150 mM NaCl and 0.1% BSA,) and aliquots are immediately snap-frozen in liquid nitrogen and stored at −80° C. Protein content of the membrane suspension is determined using the Bio-Rad protein assay kit (Bio-Rad, Hercules, Calif.).

Competitive radioligand binding assays with membrane preparations are performed in Millipore 96-well filtration plates with GF/C membrane filters which are pre-coated with 200 µl of 0.1% polyethylenimine (Sigma, St. Louis. Mo.). Prior to use, the plates are washed 3× with phosphate buffered saline solution. Membrane fraction in GnRH binding buffer (130 µl containing 25 µg protein for human and macaque receptors or 12 µg for rat receptors) are added to wells together with 20 µl of competing ligand at varying concentrations. The binding reaction is initiated by addition of radioligand (0.1 nM in 50 µl GnRH binding buffer.) The reaction is allowed to proceed for 90 min on a platform shaker at room temperature and then terminated by placing assay plate on a Millipore vacuum manifold (Millipore, Bedford, Mass.), aspirating the solvent, and washing wells twice with 200 µl ice cold phosphate buffered saline (PBS). Filters in the wells are removed and counted in a gamma counter. $K_i$ values are calculated from each competition binding curves using non-linear least square regression and corrected for radioligand concentration using the Cheng-Prusoff equation (Prism, GraphPad Software, San Diego, Calif.) assuming a radioligand affinity of 0.5 nM. Mean $K_i$ values are calculated from the antilog of the mean of the $pK_i$ values for each receptor ligand pair.

Membrane Binding Assays 3

Stably transfected human GNRH receptor RBL cells are grown to confluence. The medium is removed and the cell monolayer is washed once with DPBS. A solution of 0.5 mM EDTA/PBS ($Ca^{++}$ $Mg^{++}$ free) is added to the plate which is then incubated at 37° C. for 10 min. Cells are dislodged by gentle rapping of the flasks. The cells are collected and pelleted by centrifugation at 800 g for 10 min at 4° C. The cell pellet is then resuspended in buffer [DPBS (1.5 mM $KH_2PO_4$, 8.1 mM $Na_2HPO_4$, 2.7 mM KCl, and 138 mM NaCl) supplemented with 10 mM $MgCl_2$, 2 mM EGTA, pH=7.4 with NaOH]. Cell lysis is then performed using a pressure cell and applying $N_2$ at a pressure of 900 psi for 30 min at 4° C. Unbroken cells and larger debris are removed by centrifugation at 1200 g for 10 min at 4° C. The cell membrane supernatant is then centrifuged at 45,000 g and the resulting membrane pellet is resuspended in assay buffer and homogenized on ice using a tissue homogenizer. Protein concentrations are determined using the Coomassie Plus Protein Reagent kit (Pierce, Rockford, Ill.) using bovine serum albumin as a standard. The pellets are aliquoted and stored at −80° C. until use. Titration analysis using a range of protein concentrations determined the optimal protein concentration to be 15 μg per well final concentration.

UniFilter GF/C filter plates (Perkin Elmer, Boston Mass.) are pretreated with a solution of 0.5% polyethyleneimine in distilled water for 30 minutes. Filters are pre-rinsed with 200 μl per well of PBS, 1% BSA (Fraction V) and 0.01% Tween-20, pH=7.4) using a cell harvester (UniFilter-96 Filtermate; Packard). Membranes are harvested by rapid vacuum filtration and washed 3 times with 250 μl of ice-cold buffer (PBS, 0.01% Tween-20, pH=7.4). Plates are air dried, 50 μl scintillation fluid (Microscint 20; Packard) is added, and the plate is monitored for radioactivity using a TopCount NXT (Packard Instruments, Ill.).

Binding experiments are performed in buffer containing 10 mM HEPES, 150 mM NaCl, and 0.1% BSA, pH=7.5. Membranes are incubated with 50 μl [$^{125}$I] His$^5$, D-Tyr$^6$ GnRH (0.2 nM final concentration) and 50 μl of small molecule competitors at concentrations ranging from 30 pM to 10 μM for a total volume in each well of 200 μl. Incubations are carried out for 2 hrs at room temperature. The reaction is terminated by rapid filtration over GF/C filters as previously described. Curve fitting is performed using Excel Fit Software (IDBS, Emeryville, Calif.). The Ki values are calculated using the method of Cheng and Prusoff (Cheng and Prusoff, 1973) using a Kd value of 0.7 nM for the radioligand which was previously determined in saturation binding experiments.

Ca$^{++}$ Flux Measurement

To determine the inhibition of GnRH-stimulated calcium flux in cells expressing the human GnRH receptor, a 96-well plate is seeded with RBL cells stably transfected with the human GNRH receptor at a density of 50,000 cells/well and allowed to attach overnight. Cells are loaded for 1 hr at 37° C. in the following medium: DMEM with 20 mM HEPES, 10% FBS, 2 μM Fluo-4, 0.02% pluronic acid and 2.5 mM probenecid. Cells are washed 4 times with wash buffer (Hanks balanced salt, 20 mM HEPES, 2.5 mM probenecid) after loading, leaving 150 μl in the well after the last wash. GnRH is diluted in 0.1% BSA containing FLIPR buffer (Hanks balanced salt, 20 mM HEPES) to a concentration of 20 nM and dispensed into a 96-well plate (Low protein binding). Various concentrations of antagonists are prepared in 0.1% BSA/FLIPR buffer in a third 96-well plate. Measurement of fluorescence due to GnRH stimulated (50 μl of 20 nM, or 4 nM final) Ca$^{++}$ flux is performed according to manufacturer's instructions on a FLIPR system (Molecular Devices, FLIPR384 system, Sunnyvale, Calif.) following a 1-minute incubation with 50 μl of antagonist at varying concentrations.

Phosphoinositol Hydrolysis Assay

The procedure is modified from published protocols (W.Zhou et al; *J.Biol.Chem.* 270(32), pp18853–18857, 1995). Briefly, RBL cells stably transfected with human GNRH receptors are seeded in 24 well plates at a density of 200,000 cell/well for 24 hrs. Cells are washed once with inositol-free medium containing 10% dialyzed FBS and then labeled with 1 uCi/mL of [myo-$^3$H]-inositol. After 20–24 hrs, cells are washed with buffer (140 nM NaCl, 4 mM KCl, 20 mM Hepes, 8.3 mM glucose, 1 mM MgCl$_2$, 1 mM CaCl$_2$ and 0.1 % BSA) and treated with native GnRH peptide in the same buffer with or without various concentrations of antagonist and 10 mM LiCl for 1 hour at 37° C. Cells are extracted with 10 mM formic acid at 4° C. for 30min and loaded on a Dowex AG1-X8 column, washed and eluted with 1 M ammonium formate and 0.1 M formic acid. The eluate is counted in a scintillation counter. Data from PI hydrolysis assay are plotted using non-linear least square regression by the Prism program (Graphpad, GraphPad Software, San Diego, Calif.), from which dose ratio is also calculated. The Schild linear plot is generated from the dose-ratios obtained in four independent experiments by linear regression, and the X-intercept is used to determine the affinity of the antagonist.

Castrate Animal Studies

Studies of castrate animals provide a sensitive in vivo assay for the effects of GNRH antagonist (*Andrology* 25: 141–147, 1993). GnRH receptors in the pituitary gland mediate GnRH-stimulated LH release into the circulation. Castration results in elevated levels of circulating LH due to reduction of the negative feedback of gonadal steroids resulting in enhancement of GnRH stimulated LH release. Consequently, measurement of suppression of circulating LH levels in castrated macaques can be used as a sensitive in vivo measure of GnRH antagonism. Therefore, male macaques are surgically castrated and allowed to recover for four-weeks at which point elevated levels of LH are present. Animals are then administered the test compound as an oral or i.v. dose and serial blood samples taken for measurement of LH. LH concentrations in serum from these animals can be determined by immunoassay or bioassay techniques (*Endocrinology* 107: 902–907, 1980).

Preparation of GnRH Radioligand

The GnRH analog is labeled by the chloramine-T method. To 10 μg of peptide in 20 μl of 0.5M sodium phosphate buffer, pH 7.6, is added 1 mCi of Na$^{125}$I, followed by 22.5 μg chloramine-T in 15 μl 0.05M sodium phosphate buffer and the mixture is vortexed for 20 sec. The reaction is stopped by the addition of 60 μg sodium metabisulfite in 30 μl 0.05M sodium phosphate buffer and the free iodine is removed by passing the reaction mixture through a C-8 Sep-Pak cartridge (Millipore Corp., Milford, Mass.). The peptide is eluted with a small volume of 80% acetonitrile/ water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/0.1% TFA at −80° C. and can be used for up to 4 weeks.

RIA of LH and FSH

For determination of the LH levels, each sample medium is assayed in duplicates and all dilutions are done with RIA buffer (0.01M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 μl of sample medium diluted 1:5 or rLH standard in RIA buffer and 100 μl of [125I]-labeled rLH (~30,000 cpm) plus 100 μl of rabbit anti-rLH antibody diluted 1:187,500 and 100 μl RIA buffer. The mixture is incubated at room temperature over-night. In the next day, 100 μl of goat anti-rabbit IgG diluted 1:20 and 100 μl of normal rabbit serum diluted 1:1000 are added and the mixture incubated for another 3 hr at room temperature. The incubated tubes are then centrifuged at 3,000 rpm for 30 min and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Activity of GNRH Receptor Antagonists

Activity of GNRH receptor antagonists are typically calculated from the $IC_{50}$ as the concentration of a compound necessary to displace 50% of the radiolabeled ligand from the GNRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973). GnRH receptor antagonists of this invention have a $K_i$ of 100 μM or less. In a preferred embodiment of this invention, the GnRH receptor antagonists have a $K_i$ of less than 10 μM, and more preferably less than 1 μM, and even more preferably less than 0.1 μM (i.e., 100 nM). To this end, all compounds specifically disclosed in the Examples have $K_i$'s of less than 100 nM in one or more of Membrane Binding Assays 1 through 3 above.

The ability of the GnRH antagonists to inhibit the major drug metabolizing enzymes in the human liver, namely, CYP2D6 and CYP3A4, can be evaluated in vitro according to a microtiter plate-based fluorimetric method described by Crespi et al. (*Anal. Biochem.* 248: 188–190; 1997). AMMC (i.e., 3-[2-(N,N-Diethyl-N-methylammonium)ethyl]-7-methoxy-4-methylcoumarin) and BFC (i.e., 7-benzyloxy-4-(trifluoromethyl)coumarin) at a concentration equal to Km (that is, the concentration of substrate that produces one half of the maximal velocity) are used as marker substrates for CYP2D6 and CYP3A4, respectively. Briefly, recombinant CYP2D6 or CYP3A4 is incubated with marker substrate and NADPH generating system (consisting of 1 mM NADP+, 46 mM glucose-6-phosphate and 3 units/mL glucose-6-phosphate dehydrogenase) at 37° C., in the absence or presence of 0.03, 0.09, 0.27, 0.82, 2.5, 7.4, 22, 67 and 200 μM of a sample GNRH antagonist. Reactions are stopped by the addition of an equal volume of acetonitrile. The precipitated protein is removed by centrifugation and the clear supernatant fluid is analyzed using a microtiter plate fluorimeter. GnRH antagonists of the present invention preferably have $K_i$'s greater than 250 nM, more preferably greater than 1 μM and most preferably greater than 5 μM.

As mentioned above, the GnRH receptor antagonists of this invention have utility over a wide range of therapeutic applications, and may be used to treat a variety of sex-hormone related conditions in both men and women, as well as mammals in general. For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GNRH receptor antagonist of the present invention and a pharmaceutically acceptable carrier and/or diluent. The GnRH receptor antagonist is present in the composition in an amount which is effective to treat a particular disorder—that is, in an amount sufficient to achieve GNRH receptor antagonist activity, and preferably with acceptable toxicity to the patient. Typically, the pharmaceutical compositions of the present invention may include a GNRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GNRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GNRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

The following example is provided for purposes of illustration, not limitation. In summary, the GnRH receptor antagonists of this invention may be assayed by the general methods disclosed above, while the following Examples disclose the synthesis of representative compounds of this invention.

EXAMPLES

HPLC Methods for analyzing the samples
Retention time, $t_R$, in minutes

Method 1—Supercritical Fluid Chromatography Mass Spectrum (SFC-MS)
Column: 4.6×150 mm Deltabond Cyano 5 μM from Thermo-Hypersil-Keystone.
Mobile phase: SFC grade carbon dioxide and optima grade methanol with 1 mM disodium diethylmalonate modifier.
Temperature: 50° C.
Pressure: 120 bar
Flow Rate: 4.8 mL/min
Gradient: 5% to 55% methanol over 1.7 min and hold at 55% for 0.8 min then return to 5% in 0.1 min for total run time of 2.6 min Method 2 (HPLC-MS)
Column: Waters ODS-AQ, 2.0×50 mm
Mobile phase: A=water with 0.05% trifluoroacetic acid; B=acetonitrile with 0.05% trifluoroacetic acid
Gradient: 95% A/5% B to 5% A/95% B over 13.25 min and hold 5% A/95% B over 2 min then return to 95% A/5% B over 0.25 min.
Flow Rate: 1 mL/min
UV wavelength: 220 and 254 nM Method 3 (HPLC-MS)
Column: BHK Lab ODS-O/B, 4.6×50 mm, 5 μM
Mobile phase: A=water with 0.05% trifluoroacetic acid; B=acetonitrile with 0.05% trifluoroacetic acid
Gradient: 95% A/5% B for 0.5 min, then to 90% A/10% B for 0.05 min. from 90% A/10% B to 5% A/95% B over 18.94 min, then to 1% A/99% B over 0.05 min and hold 1% A/99% B over 2.16 min. then return to 95%/5% B over 0.50 min.
Flow Rate: 2.5 mL/min.
UV wavelength: 220 and 254 nM Method 4 (HPLC-MS)
Column: Waters ODS-AQ, 2.0×50 mm
Mobile phase: A=water with 0.05% trifluoroacetic acid; B=acetonitrile with 0.05% trifluoroacetic acid
Gradient: 95% A/5% B to 10% A/90% B over 2.25 min and hold 10% A/90% B over 1.0 min then return to 95% A/5% B over 0.1 min.
Flow Rate: 1 mL/min
UV wavelength: 220 and 254 nM Method 5 (HPLC)
Column: Agilent, Zorbax SB-C18, 5 μM, 4.6×250 mm.
Mobile phase: A=water with 0.05% trifluoroacetic acid; B=acetonitrile with 0.05% trifluoroacetic acid
Gradient: 95% A/5% B to 5% A/95% B over 50 min, then 5% A/95% B to 1% A/99% B over 0.1 min, then hold 1% A/99% for 0.8 min and back to 95% A/5% over 0.2 min, hold such gradient for 4 min.
Flow Rate: 2.0 mL/min.
UV wavelength: 220 and 254 nM Method 6 (HPLC-MS)
Column: Phenomenex Synergi 4μ Max-RP 80A, 50.0×2.0 mm
Mobile phase: A=water with 0.025% of trifluoroacetic acid; B=acetonitrile with 0.025% of trifluoroacetic acid Gradient: 95% A/5% B 0.25 min, then 95% A/5% B to 95% B/5% A over 13 min, maintaining 95% A/5% B to 95% B/5% A over 2 min, then back to 95% A/5% B in 0.25 min.
Flow Rate: 1 mL/min
UV wavelength: 220 nM and 254 nM Example 1

3-[2(R)-amino-2-phenylethyl]-5-(2-fluoro-3-methoxypheny)-1-[2-fluoro-6-(trifluoromethyl)benzyl]-6-methyl-pyridine-2,4(1H,3H)-dione

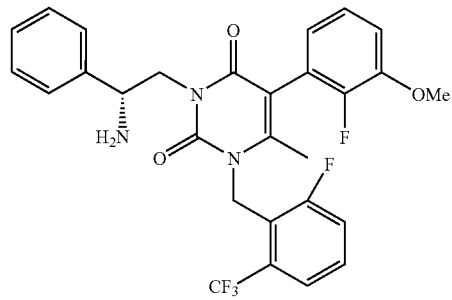

Step 1A: Preparation of 2-fluoro-6-(trifluoromethyl)benzylamine 1a

To 2-fluoro-6-(trifluoromethyl)benzonitrile (45 g, 0.238 mmol) in 60 mL of THF was added 1 M $BH_3$:THF slowly at 60° C. and the resulting solution was refluxed overnight. The reaction mixture was cooled to ambient temperature. Methanol (420 mL) was added slowly and stirred well. The solvents were then evaporated and the residue was partitioned between EtOAc and water. The organic layer was dried over $Na_2SO_4$. Evaporation gave 1a as a yellow oil (46 g, 0.238 mmol). MS (CI) m/z 194.0 ($MH^+$).

Step 1B: Preparation of N-[2-fluoro-6-(trifluoromethyl)benzyl]urea 1b

To 2-fluoro-6-(trifluoromethyl)benzylamine 1a (51.5 g, 0.267 mmol) in a flask, urea (64 g, 1.07 mmol), HCl (conc., 30.9 mmol, 0.374 mmol) and water (111 mL) were added. The mixture was refluxed for 6 hours. The mixture was cooled to ambient temperature, further cooled with ice and filtered to give a yellow solid. Recrystallization with 400 mL of EtOAc gave 1b as a white solid (46.2 g, 0.196 mmol). MS (CI) m/z 237.0 ($MH^+$).

Step 1C: Preparation of 1-[2-fluoro-6-(trifluoromethyl)benzyl]-6-methylpyrimidine-2,4(1H,3H)-dione 1c NaI (43.9 g, 293 mmol) was added to N-[2-fluoro-6-(trifluoromethyl)benzyl]urea 1b (46.2 g, 19.6 mmol) in 365 mL of acetonitrile. The resulting mixture was cooled in an ice-water bath. Diketene (22.5 mL, 293 mmol) was added slowly via dropping funnel followed by addition of TMSCl (37.2 mL, 293 mmol) in the same manner. The resulting yellow suspension was allowed to warm to room temperature slowly and was stirred for 20 hours. LC-MS showed the disappearance of starting material. To the yellow mixture 525 mL of water was added and stirred overnight. After another 20 hours stirring, the precipitate was filtered via Buchnner funnel and the yellow solid was washed with water and EtOAc to give 1c as a white solid (48.5 g, 16 mmol). $^1$H NMR (CDCl$_3$) δ 2.152 (s, 3H), 5.365 (s, 2H), 5.593 (s, 1H), 7.226–7.560 (m, 3H), 9.015 (s, 1H); MS (CI) m/z 303.0 (MH$^+$).

Step 1D: Preparation of 5-bromo-1-[2-fluoro-6-(trifluoromethyl)benzyl]-6-methylpyrimidine-2,4(1H,3H)-dione 1d Bromine (16.5 mL, 0.32 mmol) was added to 1-[2-fluoro-6-(trifluoromethyl)benzyl]-6-methylpyrimidine-2,4(1H,3H)-dione 1c (48.5 g, 0.16 mol) in 145 mL of acetic acid. The resulting mixture became clear then formed precipitate within an hour. After 2 hours stirring, the yellow solid was filtered and washed with cold EtOAc to an almost white solid. The filtrate was washed with sat.NaHCO$_3$ and dried over Na$_2$SO$_4$. Evaporation gave a yellow solid which was washed with EtOAC to give a light yellow solid. The two solids were combined to give 59.4 g of 1d (0.156 mol) total. $^1$H NMR (CDCl$_3$) δ 2.422 (s, 3H), 5.478 (s, 2H), 7.246–7.582 (m, 3H), 8.611 (s, 1H); MS (CI) m/z 380.9 (MH$^+$).

5-Bromo-1-[2,6-difluorobenzyl]-6-methylpyrimidine-2,4(1H,3H)-dione 1d.1 was made using the same procedure.

Step 1E: Preparation of 5-bromo-1-[2-fluoro-6-(trifluoromethyl)benzyl]-6-methyl-3-[2(R)-tert-butoxycarbonylamino-2-phenylethyl]-pyrimidine-2,4(1H,3H)-dione 1e To 5-bromo-1-[2-fluoro-6-(trifluoromethyl)benzyl]-6-methylpyrimidine-2,4(1H,3H)-dione 1d (15 g, 39.4 mmol) in 225 mL of THF were added N-t-Boc-D-phenylglycinol (11.7 g, 49.2 mmol) and triphenylphosphine (15.5 g, 59.1 mmol), followed by addition of di-tert-butyl azodicarboxylate (13.6 g, 59.1 mmol). The resulting yellow solution was stirred overnight. The volatiles were evaporated and the residue was purified by silica gel with 3:7 EtOAc/Hexane to give 1e as a white solid (23.6 g, 39.4 mmol). MS (CI) m/z 500.0 (MH$^+$-Boc).

Step 1F: Preparation of 3-[2(R)-amino-2-phenylethyl]-5-(2-fluoro-3-methoxyphenyl)-1-[2-fluoro-6-(trifluoromethyl)benzyl]-6-methyl-pyrimidine-2,4(1H,3H)-dione 1f To 5-bromo-1-[2-fluoro-6-(trifluoromethyl)benzyl]-6-methyl-3-[2(R)-tert-butoxycarbonylamino-2-phenylethyl]-pyrimidine-2,4(1H,3H)-dione 1e (15 g, 25 mmol) in 30 mL/90 mL of H$_2$O/dioxane in a pressure tube were added 2-fluoro-3-methoxyphenylboronic acid (4.25 g, 25 mmol) and sodium carbonate (15.75 g, 150 mmol). N$_2$ gas was bubbled through for 10 min. Tetrakis(triphenylphosphine)palladium (2.9 g, 2.5 mmol) was added, the tube was sealed and the resulting mixture was heated at 90° C. overnight. After cooling to ambient temperature, the precipitate was removed by filtration. The volatiles were removed by evaporation and the residue was partitioned between EtOAc/sat. NaHCO$_3$. The organic solvent was evaporated and the residue was chromatographed with 2:3 EtOAc/Hexane to give 13.4 g (20.8 mmol, 83%) yellow solid.

This yellow solid (6.9 g, 10.7 mmol) was dissolved in 20 mL/20 mL CH$_2$Cl$_2$/TFA. The resulting yellow solution was stirred at room temperature for 2 hours. The volatiles were evaporated and the residue was partitioned between EtOAc/sat. NaHCO$_3$. The organic phase was dried over Na$_2$SO$_4$. Evaporation gave 1f as a yellow oil (4.3 g, 7.9 mmol, 74%). $^1$H NMR (CDCl$_3$) δ 2.031 (s, 3H), 3.724–4.586 (m, 6H), 5.32–5.609 (m, 2H), 6.736–7.558 (m, 11H); MS (CI) m/z 546.0 (MH$^+$).

3-[2(R)-amino-2-phenylethyl]-5-(2-fluoro-3-methoxyphenyl)-1-[2,6-difluorobenzyl]-6-methyl-pyrimidine-2,4(1H,3H)-dione 1f.1 was made using the same procedure described in this example.

Example 2

3-[2(R)-AMINO-2-CYCLOHEXYLETHYL]-5-(2-FLUORO-3-METHOXYPHENYL)-1-[2,6-DIFLUOROBENZYL]-6-METHYL-PYRIMIDINE-2,4(1H,3H)-DIONE

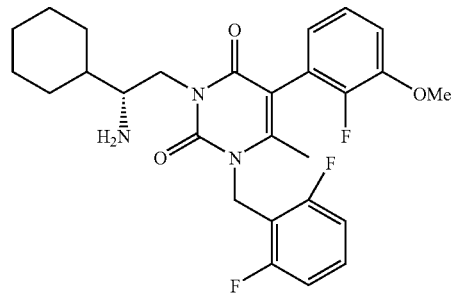

Step 2A: Preparation of tert-butyl 1-cyclohexyl-2-hydroxyethylcarbamate 2a

A solution of N-(t-butyloxycarbonyl)cyclohexylglycine (2.0 g, 7.77 mmol) in anhydrous THF (10 mL) was cooled to 0° C. Borane solution (1 M in THF, 15.5 mL, 15.5 mmol) was added slowly and the reaction mixture was warmed to room temperature and stirred for 2 hours. The reaction was quenched with MeOH (5 mL), volatiles were evaporated and the residue was partitioned between water and EtOAc. The organic layer was washed with saturated NaHCO$_3$/water, brine, dried (sodium sulfate), and evaporated to give tert-butyl 1-cyclohexyl-2-hydroxyethylcarbamate 2a (1.26 g, 66.7%), MS (CI) m/z 144.20 (MH$^+$-Boc).

Step 2B: Preparation of 5-bromo-3-[2(R)-tert-butoxycarbonylamino-2-cyclohexylethyl]-1-[2,6-difluorobenzyl]-6-methyl-pyrimidine-2,4(1H,3H)-dione 2b A solution of tert-butyl 1-cyclohexyl-2-hydroxyethylcarbamate 4a (638 mg, 2.62 mmol) in THF (10 mL) was treated with 5-bromo-1-(2,6-difluorobenzyl)-6-methylpyrimidine-2,4(1H,3H)-dione 1d.1 (869 mg, 2.62 mmol) and triphenylphosphine (1.03 g, 3.93 mmol) at ambient temperature, then di-tert-butylazodicarboxylate (906 mg, 3.93 mmol) was introduced. The reaction mixture was stirred at ambient temperature for 16 hours and volatiles were evaporated. The residue was partitioned between saturated NaHCO$_3$/H$_2$O and EtOAc. The organic layer was dried (sodium sulfate), evaporated, and purified by flash chromatography (silica, 25% EtOAc/hexanes) to give compound 2b (1.39 g, 95.4%). MS (CI) m/z 456.10, 458.10 (MH$^+$-Boc).

Step 2C: Preparation of 3-[2(R)-tert-butoxycarbonylamino-2-cyclohexylethyl]-5-(2-fluoro-3-methoxyphenyl)-1-[2,6-difluorobenzyl]-6-methyl-pyrimidine-2,4(1H,3H)-dione 2c 5-Bromo-3-[2(R)-tert-butoxycarbonylamino-2-cyclohexylethyl]-1-[2,6-difluorobenzyl]-6-methyl-pyrimidine-2,4(1H,3H)-dione 2b (1.0 g, 1.79 mmol) in bezene/EtOH/ethylene glycol dimethyl ether (20/2/22 mL) was added 2-fluoro-3-methoxyphenylboronic acid (382 mg, 2.24 mmol) and saturated Ba(OH)$_2$/water (~0.5 M, 15 mL). The reaction mixture was deoxygenated with N$_2$ for 10 minutes, tetrakis(triphenylphosine) palladium (0) (208 mg, 0.18 mmol) was added and the reaction mixture was heated at 80° C. overnight under N$_2$. The reaction mixture was partitioned between brine and EtOAc. The organic layer was dried (sodium sulfate), evaporated, and purified by flash chromatography (silica, 30% EtOAc/hexanes) to give compound 2c (348 mg, 32.3%). MS (CI) m/z 502.20 (MH$^+$-Boc).

Step 2D: Preparation of 3-[2(R)-amino-2-cyclohexylethyl]-5-(2-fluoro-3-methoxyphenyl)-1-[2,6-difluorobenzyl]-6-methyl-pyrimidine-2,4(1H,3H)-dione 2d To compound 2c (300 mg, 0.5 mmol) in dichloromethane (DCM, 2 mL) was added TFA (2 mL) and the reaction mixture was stirred at ambient temperature for 1 hour. Volatiles were evaporated and the residue was partitioned between saturated NaHCO$_3$/water and EtOAc. The organic layer was dried (sodium sulfate), evaporated, purified by reverse phase HPLC (C-18 column, 15–75% ACN/water) to give compound 2d. MS (CI) m/z 502.20 (MH$^+$).

Example 3

3-[2(R)-amino-2-phenylethyl]-5-(2-chloro-3-methyoxyphenyl)-1-[2-fluoro-6-(trifluoromethyl)benzyl]pyrimidine-2,4(1H,3H)-dione

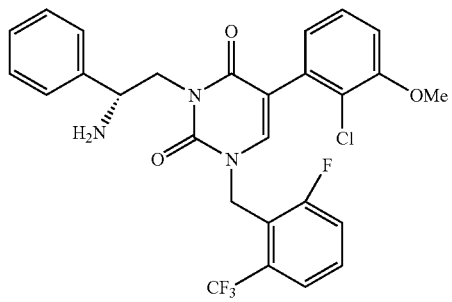

Step 3A: Preparation of 2-chloro-3-methoxybenzaldehyde 3a

To a suspension of 3-hydroxybenzaldehyde (20.12 g, 160 mmol) in HOAc (40 mL) was added carefully tBuOCl (20 mL, 176 mmol) with stirring. The reaction became a clear solution and strongly exothermic. It was allowed to cool and stirred for 16 hours, resulting in a white precipitate. The solid was filtered, washed with H$_2$O and dried to give 2-chloro-3-hydroxybenzaldehyde (13.77 g, 55%), GCMS (EI) m/z 156, 158 (M$^+$).

To a solution of 2-chloro-3-hydroxybenzaldehyde (4.55 g, 29 mmol) in DMF (30 mL) was added K$_2$CO$_3$ (4.8 g, 34.9 mmol) followed by MeI (2.7 mL, 43.6 mmol), and the mixture was stirred at room temperature for 16 hours. Following concentration in vacuo, the residual was taken up in ethyl acetate, washed with H$_2$O, brine, dried over Na$_2$SO$_4$, and concentrated. Purification by column chromatography on silica gel with ethyl acetate/hexanes 1/5 afforded 2-chloro-3-methoxybenzaldehyde 3a (4.68 g, 94%) as a colorless oil, which solidified upon standing. GCMS (EI) m/z 170, 172 (M$^+$).

Step 3B: Preparation of 2-chloro-1-methoxy-3-[2-(methylsulfanyl)-2-(methylsulfinyl)vinyl]benzene 3b To a solution of 2-chloro-3-methoxybenzaldehyde 3a (4.65 g, 27.3 mmol) and methyl (methylthio)methyl sulfoxide (4.3 mL, 43.9 mmol) in THF (25 mL) was added a 40% methanolic solution of Triton B (6.2 mL, 13.6 mmol) and the resulting solution was refluxed for 16 hours. After THF was removed, the residue was taken up in ethyl acetate, washed with 1 N HCl, H$_2$O, and brine, then was dried over Na$_2$SO$_4$, and concentrated. Purification by column chromatography on silica gel with dichloromethane afforded 2-chloro-1-methoxy-3-[2-(methylsulfanyl)-2-(methylsulfinyl)vinyl]benzene 3b (3.61 g, 48%) as a yellow oil. GCMS (EI) m/z 225 (M$^+$-Cl-16), 210 (M$^+$-Cl-OMe).

Step 3C: Preparation of ethyl (2-chloro-3-methoxyphenyl)acetate 7c

To a solution of 2-chloro-1-methoxy-3-[2-(methylsulfanyl)-2-(methylsulfinyl)vinyl]benzene 3b (3.58 g, 12.9 mmol) in ethanol (20 mL) was added a 5 M ethanolic solution of HCl (5.2 mL) and the resulting solution was refluxed for 3 hours. After evaporation, the residue was purified by column chromatography on silica gel with dichloromethane to afford ethyl (2-chloro-3-methoxyphenyl)acetate 3c (2.78 g, 94%) as a yellow oil. GCMS (EI) m/z 228, 230 (M$^+$).

Step 3D: Preparation of ethyl 2-(2-chloro-3-methoxyphenyl)-3-(dimethylamino)acrylate 3d A solution of ethyl (2-chloro-3-methoxyphenyl)acetate 3c (2.78 g, 12 mmol) in DMFDMA (16 mL, 120 mmol) was refluxed for 16 hours. After evaporation, the residue was purified by column chromatography on silica gel with ethyl acetate/hexanes 1/2 to 1/1 to afford unreacted ethyl (2-chloro-3-methoxyphenyl)acetate 3c (1.8 g, 65%) first, and then ethyl 2-(2-chloro-3-methoxyphenyl)-3-(dimethylamino)acrylate 3d (1.1 g, 32%; 90% based on recovered starting material) as a yellow syrup. MS (CI) m/z 284.0, 286.0 (MH$^+$).

Step 3E: Preparation of 5-(2-chloro-3-methoxyphenyl)pyrimidine-2,4(1H,3H)-dione 3e To a mixture of ethyl 2-(2-chloro-3-methoxyphenyl)-3-(dimethylamino)acrylate 3d (1.7 g, 6 mmol), urea (1.08 g, 18 mmol) and NaI (2.7 g, 18 mmol) in acetonitrile (20 mL) was added TMSCl (2.3 mL, 18 mmol). The resulting mixture was refluxed for 16 hours, cooled to room temperature, and 1.0 M NaOH (30 mL) was added. The resultant solution was stirred for 20 hours, and acetonitrile was removed in vacuo. The aq. solution was washed with ether, cooled in ice bath, and neutralized with 1 N HCl (30 mL). The precipitate was filtered, washed with additional H$_2$O, and dried to give 5-(2-chloro-3-methoxyphenyl)pyrimidine-2,4(1H,3H)-dione 3e (1.24 g, 82%) as a pale yellow solid. MS (CI) m/z 253.1, 255.1 (MH$^+$).-

Step 3F: Preparation of 5-(2-chloro-3-methoxyphenyl)-1-[2-fluoro-6-(trifluoromethyl)benzyl]pyrimidine-2,4(1H,3H)-dione 3f To a suspension of 5-(2-chloro-3-methoxyphenyl)pyrimidine-2,4(1H,3H)-dione 3e (2.2 g, 8.7 mmol) in acetonitrile (25 mL) was added bis(trimethylsilyl)acetamide (4.3 mL, 17.4 mmol), and the resulting solution was refluxed for 1.5 hours. The mixture was cooled to room temperature, 2-fluoro-3-trifluoromethylbenzyl bromide (2.7 g, 10.5 mmol) was added, and reflux was resumed for 16 hours. The reaction was quenched by addition of MeOH (25 mL) and stirring for 2 hours. After concentration, the residue was purified by column chromatography on silica gel with ethyl acetate/hexanes 1/1 to afford 5-(2-chloro-3-methoxyphenyl)-1-[2-fluoro-6-(trifluoromethyl)benzyl]pyrimidine-2,4(1H,3H)-dione 3f (3.3 g, 88%) as a white solid. MS (CI) m/z 429.0, 431.0 (MH$^+$).

Step 3G: Preparation of 3-[2(R)-(tert-butoxycarbonylamino)-2-phenylethyl]-5-(2-chloro-3-methoxyphenyl)-1-[2-fluoro-6-(trifluoromethyl)benzyl]pyrimidine-2,4(1H,3H)-dione 3g A mixture of 5-(2-chloro-3-methoxyphenyl)-1-[2-fluoro-6-(trifluoromethyl)benzyl]pyrimidine-2,4(1H,3H)-dione 3f (75 mg, 0.175 mmol), K$_2$CO$_3$ (72 mg, 0.525 mmol) and N-(t-butyloxycarbonyl)-D-α-phenylglycinol mesylate (0.11 g, 0.35 mmol, made from N-(t-butyloxycarbonyl)-D-α-phenylglycinol in THF followed by the addition of methanesulfonyl chloride and triethylamine) in DMF (2 mL) was heated at 75° C. for 16 hours. The reaction was diluted with ethyl acetate, washed with H$_2$O and brine, dried over Na$_2$SO$_4$ and concentrated. The residue was purified by column chromatography on silica gel with ethyl acetate/hexanes 2/3 to afford compound 3g (82 mg, 72%) as a white solid. MS (CI) m/z 548.0, 550.0 (MH$^+$-Boc).

Step 3H: Preparation of 3-[2(R)-amino-2-phenylethyl]-5-(2-chloro-3-methoxyphenyl)-1-[2-fluoro-6-(trifluoromethyl)benzyl]pyrimidine-2,4(1H,3H)-dione 3h Compound 3g (2.7 g, 4.2 mmol) was dissolved in dichloromethane (10 mL), TFA (14 mL, 175 mmol) was added, and the mixture was stirred at room temperature for 4.5 hours. After concentration, the residue was taken up in DCM and saturated aq. NaHCO$_3$ was added. The aq. layer was extracted with DCM. Combined organic extracts were dried over Na$_2$SO$_4$ and concentrated to give compound 3h (2.2 g, 96%). MS (CI) m/z 548.0, 550.0 (MH$^+$).

3-[2(R)-amino-2-phenylethyl]-5-(2-chloro-3-methoxyphenyl)-1-[2,6-difluorobenzyl]pyrimidine-2,4(1H,3H)-dione 3h.1 was prepared by substitution of the appropriate starting material using the procedures provided above.

Example 4

3-[2(R)-amino-2-(isobutyl)ethyl]-5-(2-chloro-3-methoxyphenyl)-1-[2-fluoro-6-(trifluoromethyl)benzyl]pyrimidine-2,4(1H,3H)-dione

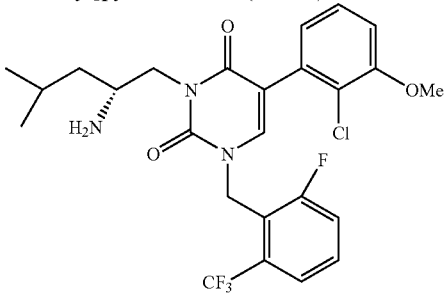

Step 4A: Preparation of 3-[2(R)-{tert-butoxycarbonyl-amino}-2-(isobutyl)ethyl]-5-(2-chloro-3-methoxyphenyl)-1-[2-fluoro-6-(trifluoromethyl)benzyl]pyrimidine-2,4(1H,3H)-dione 4a To a solution of N-(t-butyloxycarbonyl)-D-α-leucinol (1.21 g, 5.57 mmol) in pyridine (6 mL) was added tosyl chloride (1.6 g, 8.35 mmol). The reaction mixture was stirred at room temperature for 3 hours, diluted with EtOAc, and washed sequentially with 1 N HCl, H$_2$O, sat'd aq. NaHCO$_3$ and brine. The organic layer was dried over Na$_2$SO$_4$, concentrated and purified by column chromatography on silica gel with ethyl acetate/hexanes 1/3 to afford [3-methyl-1-[[[(4-methylphenyl)sulfonyl]oxy]methyl]butyl]-1,1-dimethylethyl carbamic ester (1.66 g, 80%), MS (CI) m/z 272.2 (MH$^+$-Boc).

A mixture of 5-(2-chloro-3-methoxyphenyl)-1-[2-fluoro-6-(trifluoromethyl)benzyl]pyrimidine-2,4(1H,3H)-dione 3f (56 mg, 0.13 mmol), K$_2$CO$_3$ (754 mg, 0.39 mmol) and [3-methyl-1-[[[(4-methylphenyl)sulfonyl]oxy]methyl]butyl]-1,1-dimethylethyl carbamic ester (97 mg, 0.26 mmol) in DMF (2 mL) was heated at 95° C. for 16 hours. The reaction was diluted with ethyl acetate, washed with H$_2$O and brine, dried over Na$_2$SO$_4$ and concentrated. The residue was purified by column chromatography on silica gel with ethyl acetate/hexanes 1/1 to afford recovered [3-methyl-1-[[[(4-methylphenyl)sulfonyl]oxy]methyl]butyl]-1,1-dimethylethyl carbamic ester (30 mg, 54%) and compound 4a (30 mg, 37%), MS (CI) m/z 528.0, 530.0 (MH$^+$-Boc).

Step 4B: Preparation of 3-[2(R)-amino-2-(isobutyl)ethyl]-5-(2-chloro-3-methoxyphenyl)-1-[2-fluoro-6-(trifluoromethyl)benzyl]pyrimidine-2,4(1H,3H)-dione 4b To a solution of compound 4a (30 mg, 0.048 mmol) in DCM (1 mL) was added TFA (0.1 mL, 1.3 mmol) and stirred at room temperature for 1.5 hours. After concentration, the residue was taken up in DCM and saturated aq. NaHCO$_3$ was added. The aq. layer was extracted with DCM. Combined organic extracts were dried over Na$_2$SO$_4$ and concentrated to give compound 4b. MS (CI) m/z 528.0, 530.0 (MH$^+$).

Example 5

3-[2(R)-amino-2-phenylethyl]-5-(2-fluoro-3940-methoxyphenyl)-1-[2-fluoro-6-methylsulfonylbenzyl]-6-methyl-pyrimidine-2,4(1H,3H)-dione

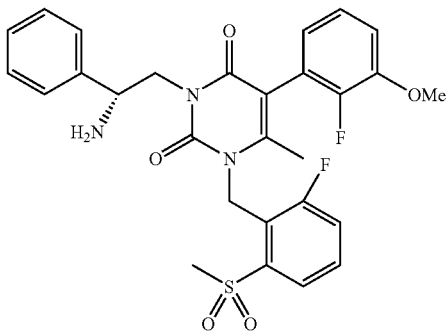

Step 5A: Preparation of 3-[2(R)-tert-butoxycarbonylamino-2-phenylethyl]-5-(2-fluoro-3-methoxyphenyl)-1-[2, 6-difluorobenzyl]-6-methyl-pyrimidine-2,4(1H,3H)-dione 5a To a solution of compound 1f.1 (28 g, 56 mmol) in dichloromethane (200 mL) was added a solution of di-tert-butyldicarbonate (12 g, 56 mmol) in dichloromethane (100 mL) dropwise through an addition funnel. The reaction mixture was stirred at room temperature for 2 hours and LC/MS indicated the starting material was consumed. The reaction mixture was concentrated by vacuum to yield the desired product 5a as a light yellow solid.

Step 5B: Preparation of 3-[2(R)-tert-butoxvcarbonylamino-2-phenylethyl]-5-(2-fluoro-3-methoxyphenyl)-1-[2-fluoro-6-methylthiobenzyl]-6-methyl-pyrimidine-2,4(1H,3H)-dione 5b To a solution of compound 5a (33 g, 56 mmol) in dry DMSO (100 mL) was added sodium thiomethoxide (4.0 g, 56 mmol) under nitrogen. The reaction mixture was heated to 100° C. under nitrogen for 1 hour. Another 0.28 eq. of sodium thiomethoxide (1.1 g, 16 mmol) was added, and the reaction mixture was heated to 100° C. under nitrogen for 1 hour. The reaction mixture was cooled and partitioned between ethyl ether and water. The organic layer was washed with saturated aqueous sodium bicarbonate solution and brine, dried with sodium sulfate, filtered and concentrated. The crude product was purified with a flash chromatography on silica gel eluted with 50% ethyl acetate in hexane to yield compound 5b as a pale yellow solid (27 g, 44 mmol, 78%).

Step 5C: Preparation of 3-[2(R)-tert-butoxycarbonylamino-2-phenylethyl]-5-(2-fluoro-3-methoxyphenyl)-1-[2-fluoro-6-methylsulfonylbenzyl]-6-methyl-pyrimidine-2,4(1H,3H)-dione 5c To a solution of compound 5b (27 g, 44 mmol) in anhydrous dichloromethane (400 mL) was added 3-chloroperoxybenzoic acid (mCPBA, 30 g, 180 mmol). The reaction mixture was stirred at room temperature overnight. The reaction mixture was partitioned between dichloromethane and water. The organic layer was washed with saturated aqueous sodium bicarbonate solution and brine, dried with sodium sulfate, filtered and concentrated. The crude product was purified with a by chromatography on silica gel eluting with 50% ethyl acetate in hexane to yield the desired product compound 5c as a pale yellow solid (15 g, 24 mmol, 53%).

Step 5D: Preparation of 3-[2(R)-amino-2-phenylethyl]-5-(2-fluoro-3-methoxyphenyl)-1-[2-fluoro-6-methylsulfonylbenzyl]-6-methyl-pyrimidine-2,4(1H,3H)-dione 5-1

To a solution of compound 5c (10 g, 15 mmol) in anhydrous dichloromethane (60 mL) was added trifluroacetic acid (TFA, 16 mL). The reaction mixture was stirred at room temperature for 4 hours. The reaction mixture was concentrated, and partitioned between ethyl acetate and diluted aqueous NaOH solution. The organic layer was washed with saturated aqueous sodium bicarbonate solution and brine, dried with sodium sulfate, filtered and concentrated to yield 5-1 as a tan solid (8.0 g, 14 mmol, 94%).

Example 6

3-[2(R)-TERT-BUTOXYCARBONYLamino-2-phenylethyl]-5-(3-HYDROXYphenyl)-1-[2-chloro-6-FLUOURObenzyl]-6-methyl-pyrimidine-2,4(1H,3H)-dione

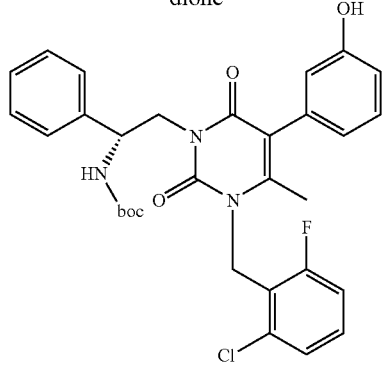

Step 6A: 3-[2(R)-tert-butoxycarbonylamino-2-phenylethyl]-5-bromo-1-[2-chloro-6-fluorobenzyl]-6-methyl-pyrimidine-2,4(1H,3H)-dione N-Boc-D-phenylglycinol (2.61 g, 11.0 mmol), 5-bromo-1-[2-chloro-6-(fluoro)benzyl]-6-methylpyrimidine-2,4(1H,3H)-dione (3.48 g, 10.0 mmol), $PPh_3$ (3.95 g, 15.0 mmol) and di-tert-butyl azodicarboxylate (3.45 g, 15.0 mmol) in 40 mL anhydrous THF were stirred at ambient temperature under $N_2$ for 16 hours. The solvent was removed in vacuo and the residue was purified via silica gel (~300 g) with EtOAc/hexanes as elutant (increasing from 10% to 30% EtOAc) to give 4.29 g (76% yield) of 6a as a foaming solid.

MS (M+H)$^+$: 466.0/468.1. NMR (CDCl$_3$), δ, 7.41–7.25 (m, 7H), 7.03–6.97 (m, 1H), 5.60 (d, J=16.3 Hz, 1H), 5.55–5.40 (m, 1H), 5.31 (d, J=16.3 Hz, 1H), 5.18–4.78 (m, 1H), 4.24–4.34 (m, 1H), 4.09 (dd, J=13.2 & 3.0 Hz, 1H), 2.46 (s, 3H), 1.37 (s, 9H).

Step 6B: 3-[2(R)-tert-butoxycarbonylamino-2-phenylethyl]-5-(3-hydroxyphenyl)-1-[2-chloro-6-fluorobenzyl]-6-methyl-pyrimidine-2,4(1H,3H)-dione Compound 6a (4.00 g, 7.06 mmol), 3-hydroxyphenylboronic acid pinacol ester (2.33 g, 10.59 mmol), K₂CO₃ (7.8 mL, 2N solution, 15.5 mmol), and Ba(OH)₂ (2.6 mL sat. solution) was suspended in 130 mL toluene and 50 mL EtOH in a tube. The mixture was purged with N₂ for 15 min, Pd(PPh₃)₄ (404 mg, 0.35 mmol) was added, the tube was sealed and heated to 100° C. for 16 hours. After cooling the mixture to room temperature, the solids were filtered and the solution was evaporated. The resulting residue was purified via silica gel (30–40% EtOAc/hexanes) to give a slightly brown foaming solid 6b (3.96 g, 98% yield). MS (M-Boc+H)⁺: 480.2/482.2. NMR (CDCl₃), δ, 7.38–7.17 (m, 8H), 7.05–6.96 (m, 1H), 6.74 (d, J=7.8 Hz, 1H), 6.68 (d, J=7.8 Hz, 1H), 6.63 (s, 1H), 5.85–4.86 (m, 4H), 4.40–4.23 (m, 1H), 4.15–3.95 (m, 1H), 1.22 (s, 3H).

3-[2(R)-tert-butoxycarbonylamino-2-phenylethyl]-5-(3-hydroxyphenyl)-1-[2-fluoro-6-trifluoromethylbenzyl]-6-methyl-pyrimidine-2,4(1H,3H)-dione, compound 6b.1 was made by the same procedure.

Example 7

3-[2(R)-amino-2-phenylethyl]-5-(2-fluoro-3-([4-hydroxycarbonyl]-1-butoxy)phenyl)-1-[2,6-difluorobenzyl]-6-methyl-pyrimidine-2,4(1H,3H)-dione

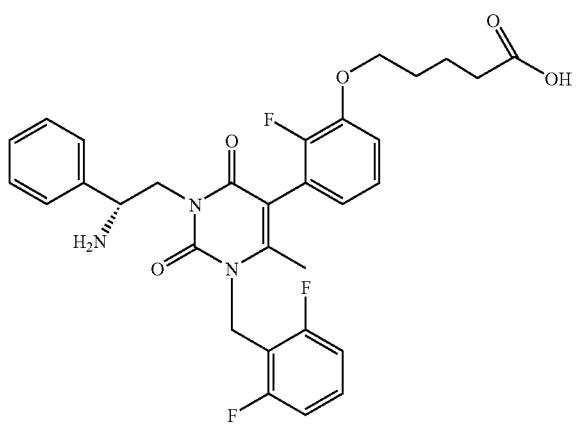

Step 7A: Preparation of 3-[2(R)-tert-butoxycarbonylamino-2-phenylethyl]-5-(2-fluoro-3-hydroxyphenyl)-1-[2,6-difluorobenzyl]-6-methyl-pyrimidine-2,4(1H,3H)-dione To 1f.1 hydrochloride (2.13 g, 4 mmol) in dry dichloromethane (20 mL) at −78° C. under N₂, was added of BBr₃ in dichloromethane (1M, 16 mL, 4 eq) slowly. The mixture was then stirred overnight while the temperature rose gradually to room temperature. Solvent and excess of BBr₃ were removed by N₂ purging which resulted in a yellow solid. The solid was dissolved in MeOH to destroy possible remaining BBr₃ and then concentrated again by N₂ purging. The resulting solid was suspended in dichloromethane (50 mL) and TEA was added until pH>8. Boc anhydride (698 mg, 0.8 eq.) was added and stirred for a few hours. TLC and HPLC-MS indicated the completion of the reaction. The mixture was concentrated and partitioned between water and ethyl acetate. The organic layer was separated, dried, and concentrated to a residue which was purified by silica gel chromatography to yield 7a (1.5 g). MS (M-Boc+H)⁺: 518.4.

Step 7B: Preparation of 3-[2(R)-tert-butoxycarbonylamino-2-phenylethyl]-5-(2-fluoro-3-([4-hydroxycarbonyl]-1-butoxy)phenyl)-1-[2,6-difluorobenzyl]-6-methyl-pyrimidine-2,4(1H,3H)-dione To the Boc protected phenol 7a (581 mg, 1.0 mmol) in anhydrous DMF (5 mL), added methyl 5-bromovalerate (234 mg, 1.2 mmol) and K₂CO₃ (690 mg, 5.0 mmol). The mixture was vigorously stirred at 50° C. for 5 hours. To the stirring mixture, LiOH (240 mg, 10 mmol) was added, followed by MeOH (10 mL) and water (10 mL). The mix was heated at 80° C. for 1 hour. The mixture was was cooled to room temperature, acidified with a sat. citric acid solution to pH=3, and was extracted with ethyl acetate. The organic layers were washed with water, dried and concentrated to yield an oil, which was purified by chromatography (hexane/ethyl acetate=1/1) to yield 7b (0.68 g, foam-like). MS (M-Boc+H)⁺: 582.1. NMR (CDCl₃), δ, 7.39–6.79 (m, 11H), 5.76 (d, J=7.5 Hz, 1H), 5.45 & 5.40 (2 m, 1H), 5.35–4.87 9 (m, 2H), 4.41–4.28 (m, 1H), 4.10–4.5 (m, 3H), 2.46–2.42 (m, 2H), 2.13 (s, 3H), 1.88–1.80 (m, 4H), 1.38 (s, 9H).

Step 7C: Preparation of 3-[2(R)-amino-2-phenylethyl]-5-(2-fluoro-3-([4-hydroxycarbonyl]-1-butoxy)phenyl)-1-[2,6-difluorobenzyl]-6-methyl-pyrimidine-2,4(1H,3H)-dione Compound 7b (0.68 g) was treated in 4N HCl in dioxane (5 mL) for 2 hours. The reaction mixture was concentrated and purified by prep HPLC. The desired compound 7-1 was initially obtained as TFA salt then was desalted on HPLC to yield free amino acid product. The sodium salt was made by suspending the 7-1 free base in 50 mL of water, then gradually adding 0.2 NaOH until all material was dissolved. pH of the solution was about 9. The solution was lyophilized to give compound 7-1 sodium salt (395 mg). MS (M+1)⁺: 582.3. NMR (DMSO-d₆), δ: 7.47–7.37 (m, 1H), 7.27–7.03 (2 m, 9H), 6.75–6.71 (m, 0.5H), 6.61–6.57 (m, 0.5H), 5.22–5.20 (m, 2H), 4.15–4.04 (m, 1H), 4.06 (t, J=5.7 Hz, 2H), 3.96–3.82 (m, 2H), 2.30 (t, J=7.5Hz, 2H), 2.13 (s, 3H), 1.78–1.63 (m, 4H).

The following compounds were made according the above procedure:

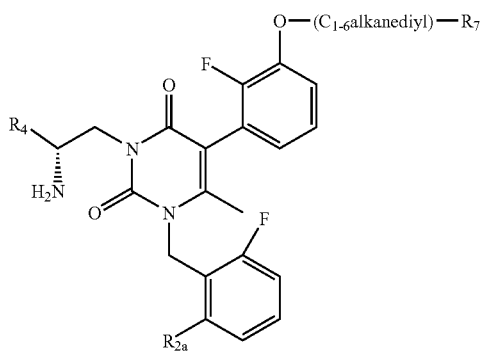
| No. | $R_{2a}$ | $R_4$ | -($C_{1-6}$alkanediyl)-$R_7$ | Mass | MW | $t_R$ (method) |
|---|---|---|---|---|---|---|
| 7-1 | F | Ph | pentanoic acid | 582.1 | 581.6 | 1.037 (1) |
| 7-2 | Cl | Ph | pentanoic acid | 598.2 | 598.0 | 8.570 (3) |
| 7-3 | $CF_3$ | Ph | pentanoic acid | 631.2 | 631.6 | 6.036 (2) |
| 7-4 | $CF_3$ | cyclopentyl | pentanoic acid | 624.2 | 623.6 | 6.390 (2) |
| 7-5 | $SO_2Me$ | Ph | butanoic acid | 628.3 | 627.7 | 5.139 (2) |
| 7-6 | $SO_2Me$ | Ph | pentanoic acid | 642.1 | 641.7 | 5.361 (2) |
| 7-7 | $CF_3$ | Ph | hexanoic acid ether | 646.3 | 645.6 | 6.320 (2) |
| 7-8 | $SO_2Me$ | Ph | hexanoic acid ether | 656.3 | 655.7 | 5.655 (2) |
| 7-9 | $CF_3$ | isobutyl | hexanoic acid ether | 626.2 | 625.6 | 1.157 (1) |
| 7-10 | $CF_3$ | isobutyl | pentanoic acid | 612.2 | 611.6 | 1.160 (1) |
| 7-11 | F | Ph | hexanoic acid ether | 596.3 | 595.6 | 5.900 (2) |

Starting with hydroxy substituted compounds such as compounds 6b and 6b.1 and following the procedure of Steps 7B and 7C, the following compounds were also made:
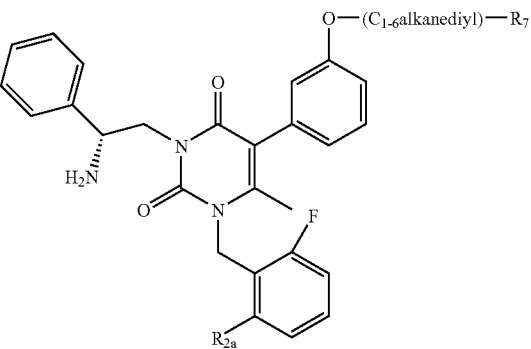
| No. | $R_{2a}$ | -($C_{1-6}$alkanediyl)-$R_7$ | Mass | MW | $t_R$ (method) |
|---|---|---|---|---|---|
| 7-12 | Cl | 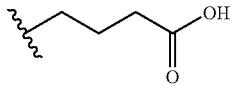 | 566.1 | 566.0 | 6.990 (2) |
| 7-13 | Cl | 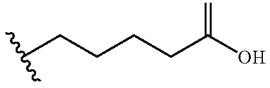 | 580.1 | 580.0 | 1.300 (1) |
| 7-14 | Cl | 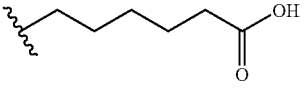 | 594.4 | 594.1 | 6.108 (2) |
| 7-15 | $CF_3$ | 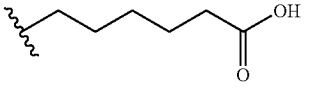 | 628.0 | 627.6 | 1.341 (1) |
| 7-16 | Cl | 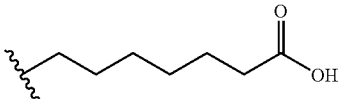 | 608.2 | 608.11 | 1.527 (1) |
| 7-17 | $CF_3$ | 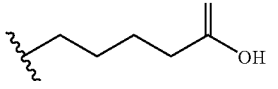 | 614.2 | 613.6 | 4.963 (2) |

Example 8

3-[2(R)-methylamino-2-phenylethyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione

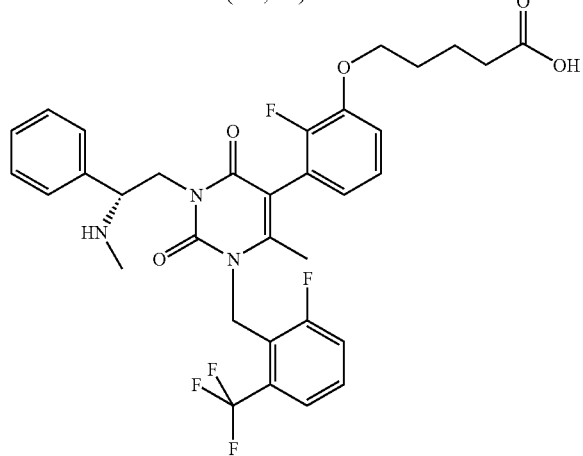

Step 8A: N-Boc-N-methyl-D-phenylglycinol

LAH (1.62 g, 5.0 eq ) was added to a round flask under nitrogen followed by the slow addition of anhydrous THF (200 mL). N-Boc-D-phenylglycinol (10 g, 42.7 mmol) was added and the reaction mixture was refluxed overnight under $N_2$. The mixture was cooled to room temperature, then to 0° C. and NaOH (10% solution) was added until it generated no bubbles. Another 200 mL of THF was added during the neutralization, then 50 g of $NaSO_4$ was added. After stirring, the mix was filtered and the solid was washed with THF. The combined solution was concentrated to yield 6.2 g of colorless oil. To the oil, di-tert-butyl dicarbonate ($Boc_2O$, 13.8 g, 5 mmol) was added. Bubbles formed right away and the mixture was diluted with toluene (10 mL) and heated at 100° C. for 0.5 hr. A short column chromatography was used to wash out $Boc_2O$ first by hexane/ethyl acetate (8/2), then hexane/ ethyl acetate (2/8) to give compound 8a (9.0 g, yield=85% ). MS (M-Boc+H)$^+$: 152.2. NMR ($CDCl_3$), δ, 7.38–7.22 (m, 5H), 5.25–5.15 (m, 1H), 4.05–4.00 (m, 2H), 2.70 (s, 3H), 1.66 (br, 1H), 1.48 (s, 9H).

Step 8B: 3-[2(R)-{N-tert-butoxycarbonyl-N-methylamino}-2-phenylethyl]-5-bromo-1-[2-fluoro-6-(trifluoromethyl)benzyl]-6-methyl-pyrimidine-2,4(1H,3H)-dione To Boc-N-methyl-D-phenyglycinol 8a (8.9 g, 35 mmol) and 5-bromo-1-[2-fluoro-6-(trifluoromethyl)benzyl]-6-methylpyrimidine-2,4(1H,3H)-dione 1d (12 g, 31.5 mmol) in dry THF, was added triphenylphosphine (12 g, 45.6 mmol), then di-tert butyl diazocarboxylate (10.5 g, 45.6 mmol). The mixture was stirred at room temperature overnight. The mix was concentrated and purified by column chromatography to yield 21 g of white foam 8b. NMR indicated it contained 50% of a byproduct (t-$BuO_2CNHNHCO_2$-tBu). MS (M-Boc+H)$^+$: 512.2, 514.2. NMR ($CDCl_3$), δ, 7.55 (d, J=7.8 Hz, 1H), 7.45–7.20 (m, 7H), 5.90–5.18 (m, 3H), 4.95–4.80 (m, 1H), 4.28 (dd, J=17.1 & 5.4 Hz, 1H), 2.56 (s, 1.5H), 2.50 (s, 3H), 2.41 (s, 1.5H), 1.42 (s, 9H).

Step 8C: 3-[2(R)-{N-tert-butoxycarbonyl-N-methylamino}-2-phenylethyl]-5-(2-fluoro-3-methoxyphenyl)-1-[2-fluoro-6-(trifluoromethyl)benzyl]-6-methyl-pyrimidine-2,4(1H,3H)-dione To the bromide 8b (2.7 g, 4.4 mmol) in a mixture of 30 mL of dioxane and 6 mL of water, was added 2-fluoro-3-methoxyphenyl boronic acid (1.48 g, 2.0 eq) and $Na_2CO_3$ (3.3 g, 7 eq.). The mixture was purged by $N_2$ gas for 15 min., then Pd(PPh$_3$)$_4$ (500 mg) was added. It was then stirred at 100° C. for 12 hours with vigorous stirring and was concentrated to remove dioxane. The mixture was partitioned in ethyl acetate and water. The organic layer was separated, dried over $Na_2SO_4$, then purified by column chromatography to yield 885 mg of 8c (33%). MS(M-Boc+H)$^+$: 560.3

Step 8D: 3-[2(R)-{N-tert-butoxycarbonyl-N-methylamino}-2-phenylethyl]-5-(2-fluoro-3-hydroxyphenyl)-1-[2-fluoro-6-(trifluoromethyl)benzyl]-6-methyl-pyrimidine-2,4(1H,3H)-dione Compound 8c (885 mg, 1.34 mmole) was dissolved in dichloromethane (50 mL), cooled to −78° C. under $N_2$, and $BBr_3$ (1M in dichloromethane, 5.2 mL, 4.0 eq ) was added slowly. The mixture was slowly warmed to room temperature with stirring overnight. The mixture was concentrated by $N_2$ flow, treated with MeOH (10 mL), and concentrated again to remove HBr. THF (50 mL) was added and triethylamine was added until the mix was basic. $Boc_2O$ (2.33 g, 0.8 eq) was added and the mixture was stirred until no free amine was seen on both TLC and HPLC. The mixture was filtered, concentrated and was partitioned in EtOAc/$H_2O$. The organic layer was separated and concentrated to give an oil, which was purified by column chromatography to give 464 mg of 8d (53% yield). MS (M-Boc+H)$^+$: 546.3. NMR ($CDCl_3$), δ, 7.55 (1H, d, J=7.8 Hz, 1H), 7.46–7.38 (m, 1H), 7.37–7.22 (m, 6H), 7.17–6.92 (m, 2H), 6.76–6.68 (m, 1H), 6.08–5.36 (m, 3H), 5.36–5.18 (m, 1H), 4.87–4.83 (m, 1H), 3.31–4.20 (m,1H), 2.70 (s, 3H), 2.16–2.10 (m, 3H), 1.42 (s, 9H).

Step 8E: 3-[2(R)-{N-tert-butoxycarbonyl-N-methylamino}-2-phenylethyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione Compound 8d (400 mg, 0.6 2 mmol) was dissolved in DMF (5 mL, anhydrous), then methyl 5-bromovalerate was added (107 microliter, 1.2 eq), followed by powder $K_2CO_3$ (430 mg, 5.0 eq). The mixture was heated at 50° C. for 3 hours. MeOH (10 mL) and water (10 mL) were added, followed by addition of LiOH (148 mg, 10 eq). The mixture was heated to 80° C. for a few hours. The mixture was cooled to r.t, acidified to pH=3 with aqueous $NaHSO_4$. The crude was partitioned in ethyl acetate/$H_2O$. The organic layer was separated, dried, purified by column chromatography (hexane/ethyl acetate 4/6) to yield 7e (300 mg, 65%). MS (M-Boc+H)$^+$: 646 3.

Step 8F: 3-[2(R)-methylamino-2-phenylethyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione Compound 8e was dissolved in 1.5 mL of dichloromethane and 1.5 mL of TFA was added. The mixture was stirred at room temperature for 1 hour, concentrated to remove TFA, partitioned in EtOAc/H₂O, and sat NaHCO₃ was added to make the aqueous solution neutral. The organic layer was separated, concentrated, and purified by chromatography (dichloromethane/MeOH 90/10 as elutant). The resulting compound 8-1 was suspended in water (20 mL) and 0.1 N NaOH was added gradually to pH=9 and sonicated constantly until all material dissolved. The solution was lyophilized to yield 120 mg of 8-1 as the sodium salt. MS (M+H)⁺: 646.4. NMR (CDCl₃), δ, 7.40 (d, J=7.5 Hz, 1H), 7.37–7.14 (m, 8H), 6.98–6.81 (m, 2H), 6.69 (t, J=7.5 Hz, 0.5H), 6.58 (t, J=6.0 Hz, 0.5H), 5.38 (s, 2H), 4.32–4.20 (m, 1H), 4.10–3.81 (m, 2H), 3.81–3.75 (m, 2H), 2.65–2.35 (br, 2H), 2.18–2.04 (m, 3H), 1.95 (s, 3H), 1.78–1.50 (m, 4H). $t_R$=1.330 (Method 1)

Example 9

3-[(1-R-1,2,3,4-tetrahydroisoquinoline)methyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione

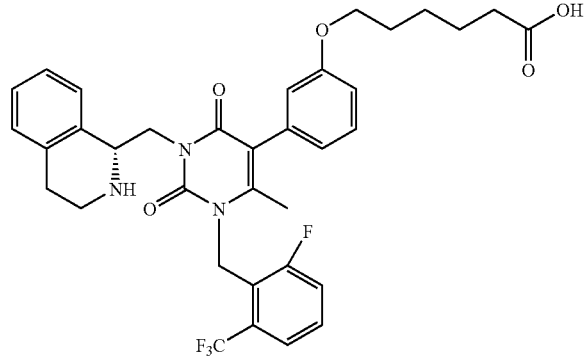

Step 9A: Preparation of 5-bromo-1-[2-fluoro-6-(trifluoromethyl)benzyl]-6-methyl-3-[N-(benzyloxycarbonyl)-1(R)-1,2,3,4-tetrahydroisoquinoline)methyl]-pyrimidine-2,4(1H,3H)-dione 9a A solution of 5-bromo-1-(2-fluoro-6-trifluoromethylbenzyl)-6-methyluracil 1d (2.29 g, 6.0 mmol) in THF (20 mL) was treated with N-(benzyloxycarbonyl)-R-1-hydroxylmethyl-1,2,3,4-tetrahydro-isoquinoline (1.96 g, 6.6 mmol, prepared from (R)-1,2,3,4-tetrahydro-1-isoquinoline carboxylic acid via the borane reduction of Step 2A) and triphenylphosphine (2.36 g, 9.0 mmol) at room temperature, then di-tert-butylazodicarboxylate (2.07 g, 9.0 mmol) was introduced in several portions over 5 min. The mixture was stirred at room temperature for 16 hr, concentrated and purified by column chromatography on silica gel eluting with ethyl acetate/hexanes 2/3 to afford compound 9a (3.96 g, 100%), MS (CI) m/z 660.2, 662.2 (MH⁺).

Step 9B: Preparation of 5-(3-hydroxyphenyl)-1-[2-fluoro-6-(trifluoromethyl)benzyl]-6-methyl-3-[N-(benzyloxycarbonyl)-1(R)-1,2,3,4-tetrahydroisoquinoline)methyl]-pyrimidine-2,4(1H,3H)-dione 9b To compound 9a (3.3 g, 5.0 mmol) in dioxane/water (90/10 mL) was added 3-hydroxyphenylboronic acid (1.38 g, 10 mmol) and Na₂CO₃ (3.18 g, 30 mmol). The mixture was deoxygenated with nitrogen for 15 min, tetrakis(triphenylphosphine) palladium (0) (0.58 g, 0.5 mmol) was added and the reaction mixture was heated at 90° C. for 16 hr. The reaction mixture was evaporated and partitioned between EtOAc and H₂O. The organic layer was washed with brine, dried over Na₂SO₄, concentrated and purified by column chromatography on silica gel with ethyl acetate/hexanes 2/3 to 1/1 to afford compound 9b (3.12 g, 93%). MS (CI) m/z 674.0 (MH⁺).

Step 9C: Preparation of 3-[N-(benzyloxycarbonyl)-(1-R-1,2,3,4-tetrahydroisoquinoline)methyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione 9c To compound 9b (168 mg, 0.25 mmol) in DMF (1 mL) was added ethyl 6-bromohexanoate (0.053 mL, 0.3 mmol) and K₂CO₃ (172 mg, 1.25 mmol). The mixture was heated at 80° C. and stirred vigorously for 5 hr. NaOH (0.1 g, 2.5 mmol) and MeOH/H₂O (1:1, 4 mL) were then added, and heated at 80° C. for 1 hr. The reaction mixture was evaporated and partitioned between EtOAc and 1N HCl (to make aq. phase pH 3). The organic layer was washed with brine, dried over Na₂SO₄, concentrated and purified by column chromatography on silica gel with ethyl acetate/hexanes 2/1 to afford compound 9c (0.14 g, 70%). MS (CI) m/z 788.3 (MH⁺).

Step 9D: Preparation of 3-[(1-R-1,2,3,4-tetrahydroisoquinoline)methyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione 9-1

Compound 9c (0.14 g, 0.18 mmol) was dissolved in 80% AcOH (10 mL) and hydrogenated under 1 atm H₂ at room temperature for 12 hr in the presence of Pd/C (14 mg). The mixture was filtered over Celite, evaporated, and partitioned between EtOAc and saturated aqueous NaHCO₃ (to make aq. phase pH 6–7). The organic layer was washed with H₂O and brine, dried over Na₂SO₄ and concentrated to afford compound 4 (0.114 g, 98%). MS (CI) m/z 654.4 (MH⁺).

The following compounds were made according to the above procedure:

| No. | -(C₁₋₆alkanediyl)-R₇ | Mass | MW | $t_R$ (method) |
|---|---|---|---|---|
| 9-1 | ⟿⟍⟋⟍⟋⟍⟋OH (C(=O)OH hexanoyl) | 654.0 | 653.67 | 6.827 (6) |

-continued

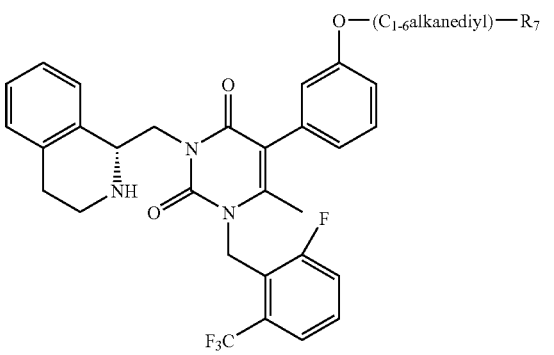

| No. | -(C$_{1-6}$alkanediyl)-R$_7$ | Mass | MW | $t_R$ (method) |
|---|---|---|---|---|
| 9-2 | (pentanoic acid) | 640.0 | 639.64 | 5.497 (6) |
| 9-3 | (butanoic acid) | 626.3 | 625.62 | 4.962 (6) |

Example 10

3-[(N-methyl-1-R-1,2,3,4-tetrahydroisoquinoline)methyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione

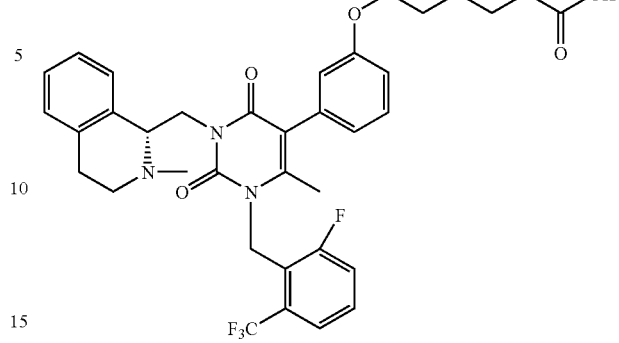

Step 10A: Preparation of 3-[(N-methyl-1-R-1,2,3,4-tetrahydroisoquinoline)methyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione 10-1

A solution of compound 9-1 (10 mg, 0.015 mmol) and formaldehyde (7.5 M solution in water; 4 µL, 0.03 mmol) in THF was stirred at RT for 5 min. Borane pyridine complex (8 M; 7.5 µL) was added and stirred for 1 hr. After concentration, the residue was purified by prep LCMS to give compound 10-1. MS (CI) m/z 668.4 (MH$^+$).

The following compounds were made according to the above procedure:

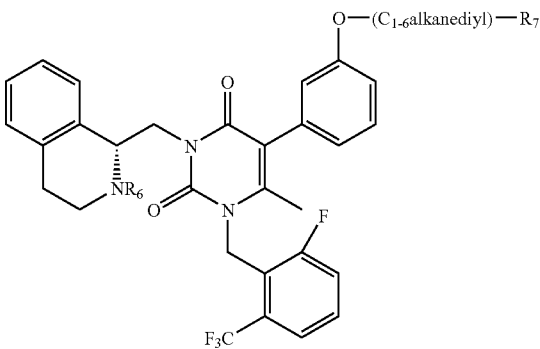

| No. | -(C$_{1-6}$alkanediyl)-R$_7$ | R$_6$ | Mass | MW | $t_R$ (method) |
|---|---|---|---|---|---|
| 10-1 | (hexanoic acid) | CH$_3$ | 668.4 | 667.70 | 6.710 (6) |
| 10-2 | (pentanoic acid) | CH$_3$ | 654.4 | 653.67 | 5.469 (6) |

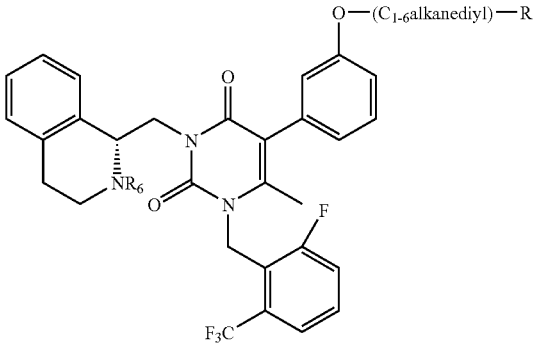

| No. | -(C$_{1-6}$alkanediyl)-R$_7$ | R$_6$ | Mass | MW | t$_R$ (method) |
|---|---|---|---|---|---|
| 10-3 | 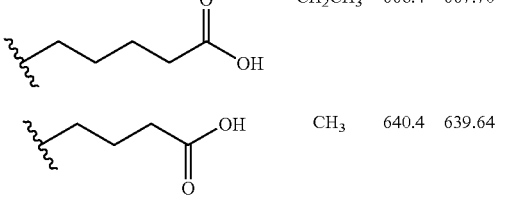 | CH$_2$CH$_3$ | 668.4 | 667.70 | 5.223 (6) |
| 10-4 | 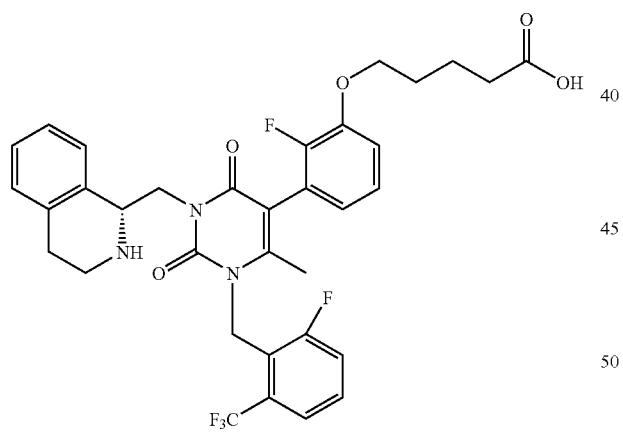 | CH$_3$ | 640.4 | 639.64 | 4.958 (6) |

Example 11

3-[(1-R-1,2,3,4-tetrahydroisoquinoline)methyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione

Step 11A: Preparation of 5-(2-fluoro-3-methoxyphenol)-1-[2-fluoro-6-(trifluoromethyl)benzyl]-6-methyl-3-[N-(benzyloxycarbonyl)-1(R)-1,2,3,4-tetrahydroisoquinoline)methyl]-pyrimidine-2,4(1H,3H)-dione 11a To compound 9a (0.66 g, 1.0 mmol) in dioxane/water (18/2 mL) was added 2-fluoro-3-methoxyphenylboronic acid (0.34 g, 2.0 mmol) and Na$_2$CO$_3$ (0.64 g, 6.0 mmol). The mixture was deoxygenated with nitrogen for 15 min, tetrakis(triphenylphosphine) palladium (0) (0.12 g, 0.1 mmol) was added and the reaction mixture was heated at 90° C. for 16 hr. The reaction mixture was evaporated and partitioned between EtOAc and H$_2$O. The organic layer was washed with brine, dried over Na$_2$SO$_4$, concentrated and purified by column chromatography on silica gel with ethyl acetate/hexanes 2/3 to 1/1 to afford compound 11a (0.57 g, 81%). MS (CI) m/z 705.9 (MH$^+$).

Step 11B: Preparation of 5-(2-fluoro-3-hydroxyphenyl)-1-[2-fluoro-6-(trifluoromethyl)benzyl]-6-methyl-3-[1(R)-1,2,3,4-tetrahydroisoquinoline)methyl]-pyrimidine-2,4(1H,3H)-dione 11b To compound 11a (1.51 g, 2.14 mmol) in dry dichloromethane (15 mL) at −78° C. was added BBr$_3$ (1M in dichloromethane, 10.7 mL, 10.7 mmol). The mixture was stirred for 16 hr while the temperature gradually rose to room temperature. The reaction mixture was evaporated by purging with nitrogen. MeOH was added and evaporated again with nitrogen. The residue was taken up in dichloromethane (5 mL) and hexane (100 mL) was added. The resultant yellow solid was filtered, washed with hexane and dried to give crude compound 11b. MS (CI) m/z 558.0 (MH$^+$).

Step 11C: Preparation of 5-(2-fluoro-3-hydroxyphenyl)-1-[2-fluoro-6-(trifluoromethyl)benzyl]-6-methyl-3-[N-(tert-butyloxycarbonyl)-1(R)-1,2,3,4-tetrahydroisoquinoline)methyl]-pyrimidine-2,4(1H,3H)-dione 11c To compound 11b in dichloromethane (15 mL) was added Et$_3$N (about 1.2 mL) until pH>8, followed by Boc$_2$O (0.37 g, 1.7 mmol). The mixture was stirred for 12 hr, evaporated and partitioned between EtOAc and H$_2$O. The organic layer was washed with brine, dried over Na$_2$SO$_4$, concentrated and purified by column chromatography on silica gel with ethyl acetate/hexanes 2/3 to 1/1 to afford compound 11c (1.2 g, 85%). MS (CI) m/z 558.0 (MH$^+$-Boc).

Step 11D: Preparation of 3-[N-(tert-butyloxycarbonyl)-1(R)-1,2,3,4-tetrahydroisoquinoline)methyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione 11-1

To compound 11c (0.17 g, 0.26 mmol) in DMF (1 mL) was added methyl 5-bromovalerate (0.044 mL, 0.31 mmol) and K$_2$CO$_3$ (0.18, 1.3 mmol). The mixture was heated at 80° C. and stirred vigorously for 5 hr. NaOH (0.1 g, 2.6 mmol) and MeOH/H$_2$O (1:1, 4 mL) were then added, and heated at 80° C. for 1 hr. The reaction mixture was evaporated and partitioned between EtOAc and 1N HCl (to make aq. phase pH 3). The organic layer was washed with brine, dried over Na$_2$SO$_4$, concentrated and purified by column chromatography on silica gel with ethyl acetate/hexanes 3/1 to afford compound 11d (0.15 g, 77%). MS (CI) m/z 658.0 (MH$^+$-Boc)

Step 11E: Preparation of 3-[(1-R-1,2,3,4-tetrahydroisoquinoline)methyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione To a solution of compound 11d (0.15 g, 0.2 mmol) in DCM (2 mL) was added TFA (0.4 mL, 5.2 mmol) and the mixture was stirred at RT for 1.5 hr. After concentration, the residue was taken up in EtOAc and saturated aqueous NaHCO$_3$ was added. The organic layer was separated, washed with brine, dried over Na$_2$SO$_4$ and concentrated to give compound 11-1 (0.11 g, 84%).MS (CI) m/z 658.0 (MH$^+$).

The following compounds were made according to the above procedure:

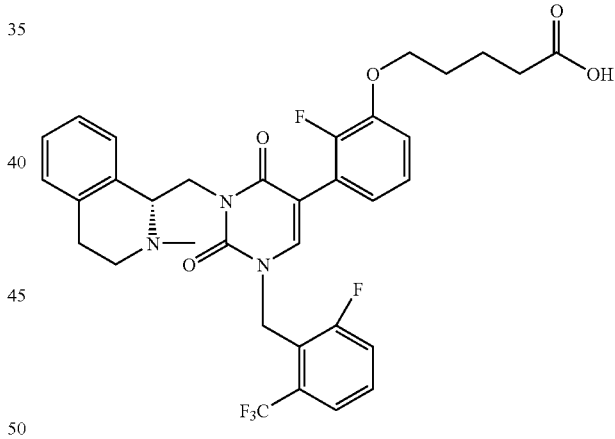

| No. | -(C$_{1-6}$alkanediyl)-R$_7$ | Mass | MW | t$_R$ (method) |
|---|---|---|---|---|
| 11-1 | (O-CH$_2$CH$_2$CH$_2$CH$_2$-C(=O)OH) | 657.9 | 657.63 | 5.490 (6) |
| 11-2 | (CH$_2$CH$_2$CH$_2$-C(=O)OH) | 644.2 | 643.61 | 5.923 (6) |

Example 12

3-[(N-methyl-1-R-1,2,3,4-tetrahydroisoquinoline)methyl]-5-(2-fluoro-3-([4-hydroxycarbonyl]-1-butoxy)phenyl)-1-[2-fluoro-6- (trifluoromethyl)benzyl]-6-methyl-pyrimidine-2,4(1H,3H)-dione

Step 12A: Preparation of 3-[(N-methyl-1-R-1,2,3,4-tetrahydroisoquinoline)methyl]-5-(2-fluoro-3-([4-hydroxycarbonyl]-1-butoxy)phenyl)-1-[2-fluoro-6-(trifluoromethyl)benzyl]-6-methyl-pyrimidine-2,4 (1H,3H)-dione 12-1

A solution of compound 11-1 (15 mg, 0.023 mmol) and formaldehyde (7.5 M solution in water; 6 μL, 0.045 mmol) in THF was stirred at room temperature for 5 min. Borane pyridine complex (8 M; 12 μL) was added and stirred for 1 hr. After concentration, the residue was purified by prep LCMS to give compound 12-1. MS (CI) m/z 672.0 (MH$^+$)

The following compounds were made according to the above procedure:

| No. | -(C$_{1-6}$alkanediyl)-R$_7$ | R$_6$ | Mass | MW | t$_R$ (method) |
|---|---|---|---|---|---|
| 12-1 | ![structure](pentanoic acid ether) | CH$_3$ | 672.0 | 671.66 | 5.672 (6) |
| 12-2 | ![structure](butanoic acid ether) | CH$_3$ | 658.2 | 657.63 | 5.924 (6) |
| 12-3 | ![structure](pentanoic acid ether) | CH$_2$CH$_3$ | 686.0 | 685.69 | 5.207 (6) |

Example 13

3-[(1-R-1,2,3,4-tetrahydroisoquinoline)methyl]-5-(2-chloro-3-([4-hydroxycarbonyl]-1-butoxy)phenyl)-1-[2-fluoro-6-(trifluoromethyl)benzyl]-pyrimidine-2,4(1H,3H)-dione

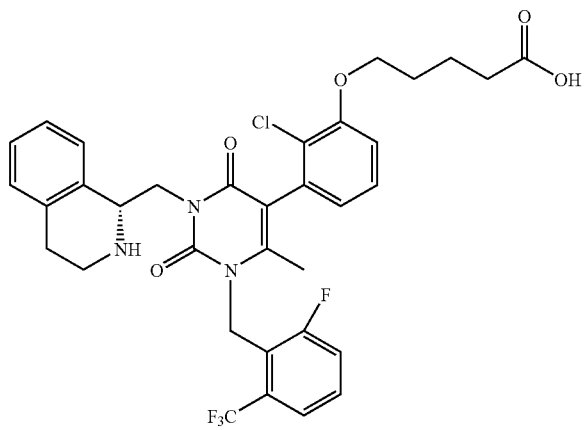

Step 13A: Preparation of N-Benzyloxycarbonyl-1-hydroxymethyl-D-1,2,3,4-tetrahydro-isoquinoline 13a To N-Benzyloxycarbonyl-D-1,2,3,4-tetrahydro-isoquinoline-1-carboxylic acid (3.11 g, 10 mmol, made from commercially available D-1,2,3,4-tetrahydro-isoquinoline-1-carboxylic acid and O-benzyloxycarbonyl-N-hydroxysuccinamide) in THF (10 mL) was added BH$_3$ (1M solution in THF; 30 mL, 30 mmol) over 5 min, and the reaction mixture was stirred for 3 hours. Acetic acid (9 mL) in MeOH (90 mL) was added and the mixture was stirred for 30 min. Solvents were evaporated, the residue was taken up in EtOAc and was washed with saturated aqueous NaHCO$_3$ (90 mL, aq. phase pH 7–8) and brine. The organic layer was dried over Na$_2$SO$_4$ and concentrated to give compound 13a (2.97 g, 100%). MS (CI) m/z 253.9 (MH$^+$-CO$_2$), 297.9 (MH$^+$); t$_R$=2.695 min (method 4).

Step 13B: Preparation of N-Benzyloxycarbonyl-1-(methanesulfonyloxymethyl)-D-1,2,3,4-tetrahydro-isoquinoline 13b To a solution of compound 13a (6.15 g, 20.7 mmol) in dichloromethane (69 mL) was added Et$_3$N (3.17 mL, 22.8 mmol) followed by methanesulfonyl chloride (1.76 mL, 22.8 mmol). The reaction was stirred at room temperature overnight, evaporated and partitioned between EtOAc and H$_2$O. The organic layer was washed with brine, dried over Na$_2$SO$_4$ and concentrated to give compound 13b (7.8 g, 100%). MS (CI) m/z 376.0 (MH$^+$); t$_R$=2.666 min (method 4).

Step 13C: Preparation of 3-[(1-R-1,2,3,4-tetrahydroisoquinoline)methyl]-5-(2-chloro-3-methoxyphenyl)-1-[2-fluoro-6-(trifluoromethyl)benzyl]-pyrimidine-2,4(1H,3H)-dione 13c Following the procedure of Step 3G, N-Benzyloxycarbonyl-1-(methanesulfonyloxymethyl)-D-1,2,3,4-tetrahydro-isoquinoline 13b (6.57 g, 17.52 mmol) and 5-(2-chloro-3-methoxyphenyl)-1-[2-fluoro-6-(trifluoromethyl)benzyl]

pyrimidine-2,4(1H,3H)-dione 3f (5.14 g, 12 mmol) formed 3-[(1-R-1,2,3,4-tetrahydroisoquinoline)methyl]-5-(2-chloro-3-methoxyphenyl)-1-[2-fluoro-6-(trifluoromethyl)benzyl]-pyrimidine-2,4(1H,3H)-dione 13c (5.73 g, 68%). MS (CI) m/z 708.0, 710.0 (MH+).

Step 13D: Preparation of 3-[(1-R-1,2,3,4-tetrahydroisoquinoline)methyl]-5-(2-chloro-3-([4-hydroxycarbonyl]-1-butoxy)phenyl)-1-[2-fluoro-6-(trifluoromethyl)benzyl]-pyrimidine-2,4(1H,3H)-dione 13-1

Following the procedure as outlined in Steps 7A to 7C and using 3-[(1-R-1,2,3,4-tetrahydroisoquinoline)methyl]-5-(2-chloro-3-methoxyphenyl)-1-[2-fluoro-6-(trifluoromethyl)benzyl]-pyrimidine-2,4(1H,3H)-dione 13c as starting material, the following compounds were synthesized.

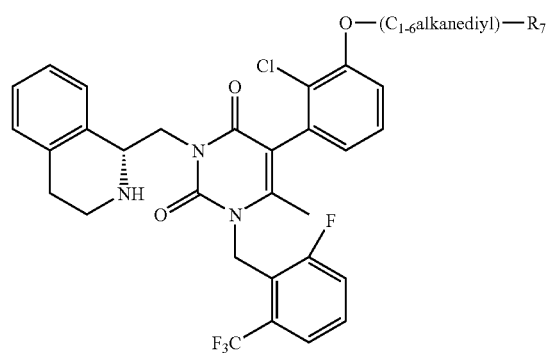

| No. | -(C$_{1-6}$alkanediyl)-R$_7$ | Mass | MW | t$_R$ (method) |
|---|---|---|---|---|
| 13-1 | | 660.4 | 660.06 | 5.376 (6) |
| 13-2 | | 646.1 | 646.03 | 22.43 (5) |
| 13-3 | | 674.1 | 674.09 | 22.52 (5) |

Example 14

3-[(1-R-1,2,3,4-tetrahydroisoquinoline)methyl]-5-(2-fluoro-3-([hydroxycarbonyl]methoxy-1-propoxy)phenyl)-1-[2-fluoro-6-(trifluoromethyl)benzyl]-6-methyl-pyrimidine-2,4(1H,3H)-dione

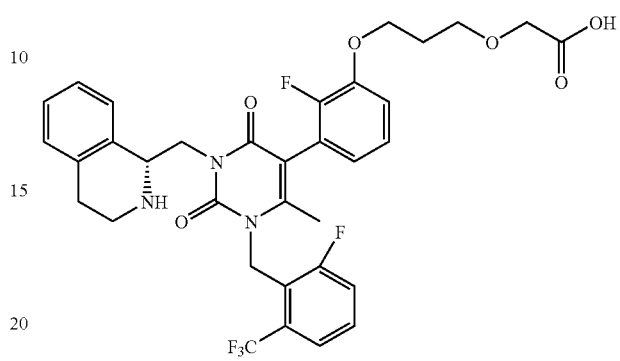

Step 14A: Preparation of 3-[(1-R-1,2,3,4-tetrahydroisoquinoline)methyl]-5-(2-fluoro-3-([3-hydroxy-1-propoxy)phenyl)-1-[2-fluoro-6-(trifluoromethyl)benzyl]-6-methyl-pyrimidine-2,4(1H,3H)-dione 14a To compound 11c (170 mg, 0.26 mmol) in DMF (1 mL) was added bromopropanol (43 mg, 0.31 mmol) and K$_2$CO$_3$ (180 mg, 1.30 mmol). The mixture was heated at 80° C. overnight. The reaction mixture was evaporated and partitioned between EtOAc and H$_2$O. The organic layer was washed with brine, dried over Na$_2$SO$_4$, concentrated and purified on prep TLC plate with ethyl acetate/hexanes 3/2 to afford compound 14a (0.13 g, 70%). MS (CI) m/z 616.0 (MH+-Boc).

Step 14B: Preparation of 3-[(1-R-1,2,3,4-tetrahydroisoquinoline)methyl]-5-(2-fluoro-3-([tert-butyloxycarbonyl]methoxy-1-propoxy)phenyl)-1-[2-fluoro-6-(trifluoromethyl)benzyl]-6-methyl-pyrimidine-2,4(1H,3H)-dione 14b To compound 14a (130 mg, 0.18 mmol) in toluene (1 mL) was added tert-butyl bromoacetate (0.04 mL, 0.27 mmol), tetrabutylammonium hydrogensulfate (3 mg, 0.009 mmol) and powdered NaOH (32 mg, 0.81 mmol). The mixture was vigorously stirred at room temperature for 24 hours and was partitioned between EtOAc and H$_2$O. The organic layer was washed with brine, dried over Na$_2$SO$_4$ and concentrated to afford crude compound 14b. MS (CI) m/z 674.0 (MH+-Boc-tBu), 730.1 (MH+-Boc).

Step 14C: Preparation of 3-[(1-R-1,2,3,4-tetrahydroisoquinoline)methyl]-5-(2-fluoro-3-([hydroxycarbonyl]methoxy-1-propoxy)phenyl)-1-[2-fluoro-6-(trifluoromethyl)benzyl]-6-methyl-pyrimidine-2,4(1H,3H)-dione 14-1

Compound 14b in dichloromethane (3 mL) was treated with TFA (0.36 mL, 4.67 mmol) at room temperature overnight, concentrated and purified on prep TLC plate with 10% MeOH in DCM to afford compound 14-1 (60 mg, 49% over 2 steps). MS (CI) m/z 674.0 (MH+).

The following compounds were made according to the above procedure:

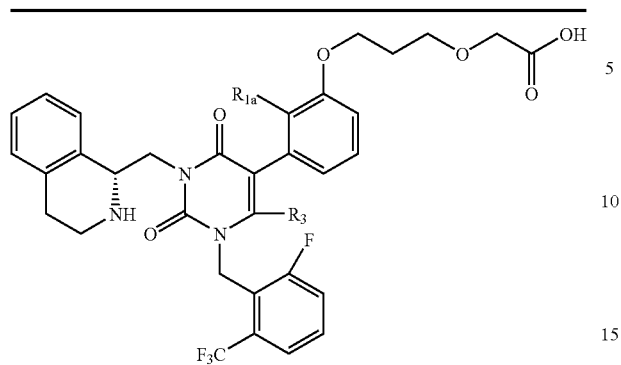

| No. | $R_{1a}$ | $R_3$ | Mass | MW | $t_R$ (method) |
|---|---|---|---|---|---|
| 14-1 | F | $CH_3$ | 674.0 | 673.63 | 6.033 (6) |
| 14-2 | Cl | H | 676.1 | 676.06 | 22.40 (5) |

It will be appreciated that, although specific embodiments of the invention have been described herein for purposes of illustration, various modifications may be made without departing from the spirit and scope of the invention. Accordingly, the invention is not limited except as by the appended claims.

We claim:

1. A compound having the following structure:

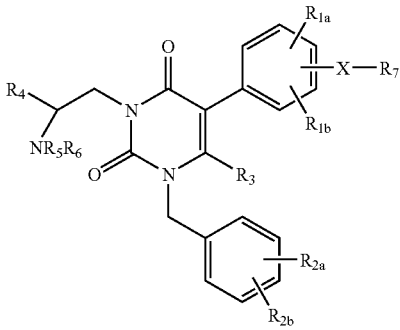

or a stereoisomer or pharmaceutically acceptable salt thereof,
wherein:
$R_{1a}$ and $R_{1b}$ are the same or different and independently hydrogen, halogen, $C_{1-4}$alkyl, or alkoxy;
$R_{2a}$ and $R_{2b}$ are the same or different and independently hydrogen, halogen, trifluoromethyl, cyano or —$SO_2CH_3$;
$R_3$ is hydrogen or methyl;
$R_4$ is phenyl or $C_{3-7}$alkyl;
$R_5$ and $R_6$ are the same or different and independently hydrogen or $C_{1-4}$alkyl; or
$R_5$ and the nitrogen to which it is attached taken together with $R_4$ and the carbon to which it is attached form 1,2,3,4-tetrahydroisoquinoline or 2,3-dihydro-1H-isoindole;
$R_7$ is —COOH or an acid isostere; and
X is —O—($C_{1-6}$alkanediyl)- or —O—($C_{1-6}$alkanediyl)—O—($C_{1-6}$alkanediyl)- wherein each $C_{1-6}$alkanediyl) is optionally substituted with from 1 to 3 $C_{1-4}$alkyl groups.

2. The compound of claim 1 wherein $R_{1a}$ is halogen.
3. The compound of claim 2 wherein $R_{1a}$ is fluoro or chloro.
4. The compound of claim 1 wherein $R_{1a}$ is hydrogen.
5. The compound of claim 1 wherein $R_{2a}$ is halogen.
6. The compound of claim 1 wherein $R_{2b}$ is trifluoromethyl, halogen or —$SO_2CH_3$.
7. The compound of claim 1 wherein $R_3$ is hydrogen.
8. The compound of claim 1 wherein $R_3$ is methyl.
9. The compound of claim 1 wherein $R_4$ is phenyl.
10. The compound of claim 1 wherein $R_4$ is $C_{3-7}$alkyl.
11. The compound of claim 10 wherein $C_{3-7}$alkyl is cyclopentyl or cyclohexyl.
12. The compound of claim 1 wherein $R_5$ is H or methyl.
13. The compound of claim 1 wherein $R_7$ is —COOH.
14. The compound of claim 1 wherein $R_7$ is an acid isostere.
15. The compound of claim 1 wherein X is a straight chain $C_{1-6}$alkanediyl.
16. The compound of claim 15 wherein the straight chain $C_{1-6}$alkanediyl is —$CH_2CH_2CH_2$—.
17. The compound of claim 15 wherein the straight chain $C_{1-6}$alkanediyl is —$CH_2CH_2CH_2CH_2$—.
18. The compound of claim 15 wherein the straight chain $C_{1-6}$alkanediyl is —$CH_2CH_2CH_2CH_2CH_2$—.
19. The compound of 1 wherein X is a branched $C_{1-6}$alkanediyl.

20. The compound of claim 1 wherein the compound is 3-[2(R)-amino-2-phenylethyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione, 3-[2(R)-amino-2-phenylethyl]-5-(3-([5-hydroxycarbonyl]-1-pentoxy)phenyl)-1-[2-fluoro-6-chlorobenzyl]-6-methyl-pyrimidine-2,4(1H,3H)-dione, 3-[2(R)-amino-2-phenylethyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione, 3-[2(R)-methylamino-2-phenylethyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione, 3-[(1-R-1,2,3,4-tetrahydroisoquinoline)methyl]-5-(3-([5-hydroxycarbonyl]-1-pentoxy)phenyl)-1-[2-fluoro-6-(trifluoromethyl)benzyl]-6-methyl-pyrimidine-2,4(1H,3H)-dione, 3-[(1-R-1,2,3,4-tetrahydroisoquinoline)methyl]-5-(2-fluoro-3-([4-hydroxycarbonyl]-1-butoxy)phenyl)-1-[2-fluoro-6-(trifluoromethyl)benzyl]-6-methyl-pyrimidine-2,4(1H,3H)-dione, 3-[(1-R-1,2,3,4-tetrahydroisoquinoline)methyl]-5-(2-fluoro-3-([3-hydroxycarbonyl]-1-propoxy)phenyl)-1-[2-fluoro-6-(trifluoromethyl)benzyl]-6-methyl-pyrimidine-2,4(1H,3H)-dione, 3-[(1-R-1,2,3,4-tetrahydroisoquinoline)methyl]-5-(2-chloro-3-([4-hydroxycarbonyl]-1-butoxy)phenyl)-1-[2-fluoro-6-(trifluoromethyl)benzyl]-pyrimidine-2,4(1H,3H)-dione or 3-[(1-R-1,2,3,4-tetrahydroisoquinoline)methyl]-5-(2-chloro-3-([5-hydroxycarbonyl]-1-pentoxy)phenyl)-1-[2-fluoro-6-(trifluoromethyl)benzyl]-pyrimidine-2,4(1H,3H)-dione.

21. A compound according to claim 13, wherein each of $R_{1a}$ and $R_{1b}$ is hydrogen.
22. The compound of claim 21, wherein $R_{2a}$ is halogen and $R_{2b}$ is halogen or trifluoromethyl.
23. The compound of claim 22, wherein $R_3$ is methyl.
24. The compound of claim 13, wherein X is —O—$C_{1-6}$ alkanediyl.
25. The compound of claim 24, wherein $R_4$ is phenyl, cyclohexyl or cyclopentyl.
26. The compound of claim 25, wherein each of $R_5$ and $R_6$ is hydrogen.
27. The compound of claim 13, wherein:
$R_{1a}$ is hydrogen;
$R_{1b}$ is hydrogen;
$R_{2a}$ is halogen;
$R_{2b}$ is halogen or trifluoromethyl;
$R_3$ is methyl; and
X is —O—$C_{1-6}$ alkanediyl.
28. The compound of claim 27, wherein $R_4$ is phenyl, cyclohexyl or cyclopentyl, and $R_5$ is hydrogen or methyl.
29. The compound of claim 28, wherein $R_4$ is phenyl.
30. The compound of claim 29, wherein $R_{2b}$ is trifluoromethyl.
31. The compound of claim 30, wherein X is —O—($CH_2CH_2CH_2CH_2CH_2$)-.
32. The compound of claim 31, wherein $R_5$ is hydrogen.
33. The compound of claim 32, wherein $R_6$ is hydrogen.
34. A pharmaceutical composition comprising a compound of claim 1 and a pharmaceutically acceptable carrier or diluent.
35. A pharmaceutical composition comprising a compound of claim 13 and a pharmaceutically acceptable carrier or diluent.
36. A pharmaceutical composition comprising a compound of claim 20 and a pharmaceutically acceptable carrier or diluent.

37. A pharmaceutical composition comprising a compound of claim 27 and a pharmaceutically acceptable carrier or diluent.

38. A pharmaceutical composition comprising a compound of claim 31 and a pharmaceutically acceptable carrier or diluent.

39. A pharmaceutical composition comprising a compound of claim 33 and a pharmaceutically acceptable carrier or diluent.

* * * * *